US011145224B2

(12) United States Patent
Cho

(10) Patent No.: US 11,145,224 B2
(45) Date of Patent: Oct. 12, 2021

(54) BLOOD FLOW SIMULATION METHOD AND APPARATUS FOR SUBJECT-SPECIFIC BLOOD VESSEL

(71) Applicant: AI MEDIC INC., Seoul (KR)

(72) Inventor: Han Yong Cho, Yongin-si (KR)

(73) Assignee: AI MEDIC INC., Seoul (KR)

( * ) Notice: Subject to any disclaimer, the term of this patent is extended or adjusted under 35 U.S.C. 154(b) by 0 days.

(21) Appl. No.: 17/055,010

(22) PCT Filed: Sep. 2, 2020

(86) PCT No.: PCT/KR2020/011737
§ 371 (c)(1),
(2) Date: Nov. 12, 2020

(87) PCT Pub. No.: WO2021/075713
PCT Pub. Date: Apr. 22, 2021

(65) Prior Publication Data
US 2021/0256877 A1 Aug. 19, 2021

(30) Foreign Application Priority Data
Oct. 15, 2019 (KR) ................ 10-2019-0127718

(51) Int. Cl.
*G09B 23/30* (2006.01)
*G16H 50/50* (2018.01)
*A61B 5/026* (2006.01)
*A61B 5/00* (2006.01)

(52) U.S. Cl.
CPC ............ *G09B 23/303* (2013.01); *A61B 5/026* (2013.01); *A61B 5/7275* (2013.01); *G16H 50/50* (2018.01)

(58) Field of Classification Search
CPC .... G09B 23/303; G16H 50/50; A61B 5/7275; A61B 5/026
See application file for complete search history.

(56) References Cited

U.S. PATENT DOCUMENTS 7,191,110 B1    3/2007  Charbel et al.
8,157,742 B2 *  4/2012  Taylor .............. G16H 50/50
                                                600/504
(Continued)

FOREIGN PATENT DOCUMENTS

KR    10-2014-0120235 A    10/2014
KR    10-2016-0026808 A     3/2016
(Continued)

OTHER PUBLICATIONS

Vignon-Clementel et al.,"Outflow boundary conditions for 3D simulations of non-periodic blood flow and pressure fields in deformable arteries", Research, 2010, pp. 625-640, vol. 13(5).
(Continued)

*Primary Examiner* — Ryan W Sherwin
(74) *Attorney, Agent, or Firm* — Novick, Kim & Lee, PLLC; Jae Youn Kim

(57) ABSTRACT

In a simulation method according to the present invention, when performing a blood flow simulation by coupling a CFD model and an LPM model, a blood flow simulation for the CFD model is performed under a set initial condition and a boundary condition, a blood flow rate Qi for each outlet and a total outflow blood flow Qtot_cfd of the CFD model are calculated by a blood flow simulation, the microvascular bed parameters of the LPM model are updated using the blood flow rate for each outlet and the total outflow blood flow of the CFD model, the boundary condition of an outlet of the CFD model is updated using the updated LPM model, and the simulation is repeatedly performed until a convergence condition of the blood flow simulation for the CFD model is satisfied, thereby calculating blood flow information for the three-dimensional blood vessel model.

13 Claims, 13 Drawing Sheets

(56) References Cited

U.S. PATENT DOCUMENTS

| | | | |
|---|---|---|---|
| 10,658,085 B2* | 5/2020 | Shim | A61B 6/504 |
| 10,971,271 B2* | 4/2021 | Itu | G16H 50/50 |
| 11,031,136 B2* | 6/2021 | Grass | G16H 10/60 |
| 2012/0041301 A1* | 2/2012 | Redel | A61B 6/4441 |
| | | | 600/425 |
| 2012/0041318 A1* | 2/2012 | Taylor | G06K 9/46 |
| | | | 600/504 |
| 2013/0132054 A1* | 5/2013 | Sharma | G16B 5/00 |
| | | | 703/9 |
| 2017/0032097 A1* | 2/2017 | Itu | G16H 50/50 |
| 2018/0089829 A1* | 3/2018 | Zhong | A61B 6/507 |
| 2020/0100705 A1* | 4/2020 | Dellimore | A61B 5/721 |

FOREIGN PATENT DOCUMENTS

| | | |
|---|---|---|
| KR | 10-1986424 B1 | 6/2019 |
| KR | 10-2020-0027660 A | 3/2020 |
| WO | 2012-021307 A2 | 2/2012 |

OTHER PUBLICATIONS

Spaan, J.A.E. et al., "Physiological basis of clinically used coronary Hemodynamic Indices", Circulation, 2006, pp. 446-455, vol. 113.

Ostergaard et al., "The role of capillary transit time heterogeneity in myocardial oxygenation and ischemic heart disease", Basic Res Cardiol, May 2014, pp. 1-18, 109(3): 409.

Monahan et al., "Pulmonary transit time from contrast echocardiography and cardiac magnetic resonance imaging: Comparison between modalities and the impact of region of interest characteristics", Echocardiography, Jan. 2019, pp. 119-124, vol. 36(1).

Taylor et al., "Computational fluid dynamics applied to cardiac computed tomography for noninvasive quantification of fractional flow reserve", scientific basis, J Am Coll Cardiol, Jun. 4, 2013, pp. 2233-2241, vol. 61(22).

Kwon et al., "A novel patient-specific model to compute coronary fractional flow reserve", Prog Biophys Mol Biol, Sep. 2014, pp. 48-55, vol. 116(1).

Liu et al., "Functional assessment of cerebral artery stenosis: A pilot study based on computational fluid dynamics", J Cereb Blood Flow Metab, Jul. 2017, pp. 2567-2576, vol. 37(7).

Shim et al., "Numerical analysis of blood flow through a stenosed artery using a coupled, multiscale simulation method", Comput Cardiol, 2000, pp. 219-222, vol. 27.

Shim et al., "Numerical analysis of three-dimensional Bjrk-Shiley valvular flow in an aorta", J Biomech Eng, Feb. 1997, pp. 45-51, vol. 119(1).

Lee et al., "Physiome approach for the analysis of vascular flow reserve in the heart and brain", Pflugers Arch, Jun. 2017, pp. 613-628, vol. 469(5-6).

* cited by examiner

BLOOD FLOW SIMULATION METHOD AND APPARATUS FOR SUBJECT-SPECIFIC BLOOD VESSEL

TECHNICAL FIELD

The present invention relates to a blood flow simulation method and apparatus for a subject-specific blood vessel. More specifically, the present invention pertains to a novel method and apparatus for performing a blood flow simulation with respect to a subject-specific three-dimensional blood vessel model by coupling a CFD model and an LPM model.

BACKGROUND ART

A fluid dynamics technique called a computational fluid dynamics (CFD) is used to obtain information about a blood flow in a blood vessel. The CFD technique is a technique that simulates a blood flow with respect to a three-dimensional blood vessel model by setting a boundary condition at the boundary of a three-dimensional blood vessel model and applying the laws of physics relating to hydrodynamics. By performing a blood flow simulation on the three-dimensional blood vessel model, it is possible to obtain information about a blood flow in the three-dimensional blood vessel model, for example, a pressure, a velocity, a flow rate, and the like. In addition, by performing the blood flow simulation on the three-dimensional blood vessel model, it is possible to obtain not only information about a blood flow, but also wall shear stress (WSS) generated on a blood vessel wall.

When information about a blood flow is obtained by blood flow simulation, it is possible to evaluate the clinical significance of a pathological change in a blood vessel such as stenosis or aneurysm. For example, the information about a blood flow may be used to predict the coronary artery fractional flow reserve (FFR) for a coronary artery stenosis, or to predict the risk of rupture for an aneurysm formed in a blood vessel.

In order to perform a blood flow simulation for a subject-specific blood vessel, a three-dimensional blood vessel model for a subject-specific blood vessel is required. The three-dimensional blood vessel model for a subject-specific blood vessel may be obtained by processing three-dimensional medical image data for a subject. The subject may be a patient suspected of vascular disease or a general public who wishes to check a health condition. The three-dimensional medical image data may include, but is not limited to, a CT (Computed Tomography) image volume or an MRI (Magnetic Resonance Imaging) image volume. Any three-dimensional medical image data such as an ultrasound image or the like may be used. A technique of obtaining a three-dimensional blood vessel model from three-dimensional medical image data is referred to as segmentation. There are known various techniques of automatically or semi-automatically segmenting a blood vessel by processing three-dimensional medical image data. In recent years, techniques that make use of machine learning, especially deep learning, have been developed. In particular, Patent Document 1] discloses a method of automatically segmenting a blood vessel from three-dimensional medical image data by combining a deep running technique and a numerical value calculation algorithm.

Furthermore, in order to perform a blood flow simulation for a subject-specific blood vessel, it is required to use not only the subject-specific three-dimensional blood vessel model but also subject-specific physiological data such as a blood pressure, a heart rate, a cardiac output and the like. In addition, it is also required to use subject-specific boundary conditions which are applied to an inlet, an outlet and a vessel wall of the subject-specific three-dimensional blood vessel model. In order to obtain the subject-specific boundary conditions for the inlet and outlet of the three-dimensional blood vessel model, the blood flow pressures or the blood flow velocities (or the blood flow rates) at the inlet and outlet may be measured, and the blood flow simulation for a subject-specific three-dimensional blood vessel model may be performed. Instead of measuring the blood flow pressures or the blood flow velocities (or the blood flow rates), there is known a method of obtaining boundary conditions in association with a lumped parameter model (LPM model). The method using the lumped parameter model is a method of modeling and analyzing the characteristics of a blood flow with an electric circuit. The method performs modeling of a blood flow with factors such as resistance (R), compliance (C) and the like.

In the analysis of a hemodynamic system for a blood vessel system, a method of performing a blood flow simulation for a three-dimensional blood vessel model by coupling a CFD model and an LPM model is widely known. In particular, there is known a method of obtaining an outlet boundary condition of a three-dimensional blood vessel model by coupling an LPM model to a microvascular bed connected to an outlet of the three-dimensional blood vessel model. The LPM model of the microvascular bed is obtained by modeling the hemodynamic characteristics of the microvascular bed with a combination of resistance (R) and compliance (C).

Non-Patent Document 1 discloses a patient-specific modeling method for a blood flow and a blood pressure in a coronary artery. In particular, Non-Patent Literature 1 discloses a method of obtaining a boundary condition by coupling a lumped parameter coronary artery microvascular bed model to the outlets of a patient-specific three-dimensional coronary artery model. FIG. 1 shows a lumped parameter coronary artery microvascular bed model linked to an outlet of a coronary artery, which is disclosed in Non-Patent Document 1. As shown in FIG. 1, the coronary artery microvascular bed model includes coronary artery resistance (Ra), coronary artery compliance (Ca), coronary capillary resistance (Ra-micro), myocardial compliance (Cim), coronary vein capillary resistance (Rv-micro), coronary vein resistance (Rv) and internal myocardial pressure (Pim(t)). In Non-Patent Document 1, it is described that the values of patient-specific parameters such as resistance and compliance of a lumped parameter model are obtained by referring to literature data based on a blood flow and a blood pressure. However, Non-Patent Document 1 does not specifically describe a method of obtaining patient-specific parameter values.

Patent Document 2 discloses a blood flow simulation method for a patient-specific cerebrovascular model. The method disclosed in Patent Document 2 is a simulation method of obtaining a patient-specific cerebrovascular model through the use of patient's MRI image data, and replacing and coupling a microvascular bed connected to the outlet of the cerebrovascular model with a lumped parameter resistance-compliance-resistance (RCR) model. Patient-specific parameter values (resistance and compliance) used in the simulation are obtained by the blood flow measured using a phase contrast magnetic resonance angiographic (PCMRA) image.

Patent Document 3 discloses a blood flow modeling method for a patient-specific coronary artery. In particular, Patent Document 3 discloses a method of obtaining the hemodynamic characteristics of a microvascular bed of a coronary artery based on a myocardial mass. FIG. 2 is a schematic diagram showing a method of simulating hemodynamics of a coronary artery by coupling a CFD model and an LPM model, which is disclosed in Patent Document 3. Referring to FIG. 2, a lumped-parameter coronary model is applied as a boundary condition to an outlet a-m of a coronary artery. In order to apply the boundary condition to the outlet of the coronary artery, it is necessary to determine the values of the parameters (Ra, Ca, Ra-micro, LVP, Cim and Rv) of the lumped-parameter model. In order to obtain the parameter values of a patient-specific LPM model, a patient's coronary artery blood flow rate Q is obtained from an equation $Q \propto Q_o M^\alpha$ (where Qo is a preset constant, and $\alpha$ is a preset scaling index) according to the physiological law experimentally derived from myocardial mass M. The total resistance R of the coronary artery is obtained based on the cross-sectional area of each outlet. The resistance connected to each outlet is obtained from an equation $Ri \propto Ri,odi^\beta$ according to the experimentally derived physiological law (where Ri,o is a preset constant, di is an outlet diameter, and $\beta$ is a preset power exponent which is a value between −3 and −2). Although Patent Document 3 describes that other parameter values are obtained experimentally, it is not explicitly described by which experiment the values are obtained. Moreover, in order to apply the method disclosed in Patent Document 3, it is necessary to obtain a patient-specific myocardial mass. The patient-specific myocardial mass is obtained by segmenting cardiac CT. image data to obtain a three-dimensional shape model of a heart, obtaining a myocardial volume from the three-dimensional shape model of the heart, and multiplying the myocardial volume by a myocardial density.

In addition, Patent Document 4 discloses a method of obtaining hemodynamic characteristics of a microvascular bed connected to an outlet of a three-dimensional blood vessel model based on the length of a coronary artery. FIG. 3 is a schematic diagram showing a method of performing a hemodynamic simulation of a coronary artery by coupling a CFD model and an LPM model, which is disclosed in Patent Document 4. The three-dimensional blood vessel model of the embodiment disclosed in Patent Document 4 is a three-dimensional coronary artery model obtained by segmenting only the coronary artery from CT image data. A pressure pattern obtained by measuring a patient's blood pressure is used as an inlet boundary condition of the three-dimensional coronary artery model. An outlet boundary condition of the three-dimensional coronary artery model is determined in association with an LPM model. As shown in FIG. 3, the calculated flow rate of a blood flowing out to the outlet of the CFD model is provided to a lumped-parameter model (LPM model) by the hemodynamic simulation for the CFD model. In the LPM model, the pressure at the outlet of the coronary artery corresponding to the calculated flow rate is calculated and provided again to the CFD model. The pressure provided to the CFD model is used as an outlet boundary condition of the CFD model for the next step calculation in the CFD model.

In particular, the method of Patent Document 4 uses the lengths of coronary artery branches to obtain patient-specific parameter values of an LPM model. The length of each of the coronary artery branches (RCA, LAD and LCX) is obtained from a three-dimensional shape model of the coronary artery. With the ratio of the lengths of the coronary artery branches, the ratio of the blood flow rates in the coronary artery branches can be calculated using the following equation.

$$Q_{LAD} : Q_{LCX} : Q_{RCA} = l_{LAD} : l_{ICX} : \frac{1}{\alpha/(l_{RCA})_{RV} + 1/(l_{RCA})_{IV}}$$

In the above equation, $\alpha$ is the right ventricle blood supply vessel correction factor, $Q_{LAD}$ is the blood flow rate in the left anterior descending coronary artery (LAD), $l_{LAD}$ is the length of the left anterior descending coronary artery, $Q_{LCX}$ is the blood flow rate in the left circumflex coronary artery (LCX), $l_{LCX}$ is the length of the left circumflex coronary artery, $Q_{RCA}$ is the blood flow rate in the right coronary artery (RCA), $l_{RCA}$ is the length of the right coronary artery, $(l_{RCA})_{RV}$ is the length of the right ventricle blood supply portion of the right coronary artery, and $(l_{RCA})_{LV}$ is the length of the left ventricle blood supply portion of the right coronary artery. By obtaining the ratio of the blood flow rates in the respective coronary artery branches, it is possible to obtain a resistance in each of the coronary artery branches (a resistance value of the LPM model).

PRIOR ART DOCUMENT

Patent Document

Patent Document: Korean Patent Application No. 10-2018-0105726 entitled "METHOD AND SYSTEM FOR AUTOMATICALLY SEGMENTING BLOOD VESSELS IN MEDICAL IMAGES USING MACHINE LEARNING AND IMAGE PROCESSING ALGORITHM"

Patent Document 2: U.S. Pat. No. 7,191,110 entitled "PATIENT-SPECIFIC CIRCULATION MODEL"

Patent Document 3: International Publication No. WO2012/021307 entitled "METHOD AND SYSTEM FOR PATIENT-SPECIFIC MODELING OF BLOOD FLOW"

Patent Document 4: Korean Patent No. 10-1986424 entitled "METHOD FOR DETERMINING PATIENT-SPECIFIC BLOOD VESSEL INFORMATION"

Non-Patent Document

Non-Patent Document 1: Vignon-Clementel et al., "Outflow boundary conditions for 3D simulations of non-periodic blood flow and pressure fields in deformable arteries", 13(5), pp. 625 to 640(2010)

Non-Patent Document 2: Spaan, J. A. E. et al., Physiological basis of clinically used coronary hemodynamic indices, Circulation 2006; 113: 446-455

Non-Patent Document 3: Ostergaard L, Kristiansen S B, Angleys H, Frøkær J, Michael Hasenkam J, Jespersen S N, Bøtker HE. The role of capillary transit time heterogeneity in myocardial oxygenation and ischemic heart disease, Basic Res Cardiol 2014 May; 109(3): 409

Non-Patent Document 4: Monahan K, Coffin S, Lawson M, Saliba L, Rutherford R, Brittain E, Pulmonary transit time from contrast echocardiography and cardiac magnetic resonance imaging: Comparison between modalities and the impact of region of interest characteristics, Echocardiography 2019 January; 36(1): 119-124

Non-Patent Document 5: Taylor C A, Fonte T A, Min J K. Computational fluid dynamics applied to cardiac computed tomography for noninvasive quantification of fractional flow reserve: scientific basis, J Am Coll Cardiol 2013 Jun. 4; 61(22): 2233-41

Non-Patent Document 6: Kwon S S, Chung E C, Park J S, Kim G T, Kim J W, Kim K H, Shin E S, Shim E B, A novel patient-specific model to compute coronary fractional flow reserve, Prog Biophys Mol Biol. 2014 September; 116(1): 48-55

Non-Patent Document 7: Liu J, Yan Z, Pu Y, Shiu W S, Wu J, Chen R, Leng X, Qin H, Liu X, Jia B, Song L, Wang Y, Miao Z, Wang Y, Liu L, Cai X C, Functional assessment of cerebral artery stenosis: A pilot study based on computational fluid dynamics, J Cereb Blood Flow Metab, 2017 July; 37(7): 2567-2576

Non-Patent Document 8: Shim E B, Kamm R D, Heldt T, Mark R G, Numerical analysis of blood flow through a stenosed artery using a coupled, multiscale simulation method, Comput Cardiol, 2000; 27: 219-22

Non-Patent Document 9: Shim E B, Chang K S. Numerical analysis of three-dimensional Bjrk-Shiley valvular flow in an aorta, J Biomech Eng, 1997 February; 119(1): 45-51

Non-Patent Document 10: Lee K E, Ryu A J, Shin E S, Shim E B, Physiome approach for the analysis of vascular flow reserve in the heart and brain, Pflugers Arch, 2017 June; 469(5-6): 613-628

In order to increase the accuracy of a hemodynamic simulation for a subject-specific three-dimensional blood vessel model, it is necessary to use a precisely-segmented three-dimensional blood vessel model. That is, the hemodynamic simulation should be performed using a three-dimensional blood vessel model having the same dimension and shape as those of a subject. In addition, the boundary conditions of the inlet and outlet of the three-dimensional blood vessel model should be accurate. That is, the pressure and blood flow velocity (or blood flow rate) equal to the pressure or blood flow velocity (or blood flow rate) at the inlet and outlet of an actual blood vessel of a subject need to be provided as the boundary conditions of the three-dimensional blood vessel model. As disclosed in Patent Document 4 described above, when the blood pressure measured from the subject is used as the inlet boundary condition of the three-dimensional blood vessel model and when the outlet boundary condition is determined in association with the LPM model, the blood pressure measurement value needs to be accurate and the parameter values of the LPM model need to be consistent with the hemodynamic characteristics of the capillary bed.

The accuracy of the subject's three-dimensional blood vessel model depends on a segmentation technique. When a subject-specific blood vessel is segmented by the method disclosed in Patent Document 1, it may be possible to obtain a subject-specific three-dimensional blood vessel model that provides a level of accuracy applicable to clinical practice. In addition, the blood pressure measured from the subject may be used as the inlet boundary condition of the subject-specific three-dimensional blood vessel model to perform the simulation. However, when the hemodynamic simulation is performed by associating the outlet boundary condition of the subject-specific three-dimensional blood vessel model with the LPM model, accurate subject-specific parameters should be obtained and used in the LPM model to ensure the accuracy of the blood flow simulation.

As a method of non-invasively obtaining subject-specific parameters of an LPM model, there are known a method of obtaining subject-specific parameters using a myocardial mass, which is disclosed in Patent Document 3, and a method of obtaining subject-specific parameters by using the length of a blood vessel, which is disclosed in Patent Document 4. However, there is a problem in that the subject-specific parameter values of the LPM model obtained by the above two methods fail to reflect the physiological phenomenon that the hemodynamic characteristics of a microvascular bed is changed due to a change in the shape of a blood vessel (especially, stenosis generation).

Non-Patent Document 2 is a document that provides the basis for the above argument. Non-Patent document 2 discloses an experimental result which indicates that a stenosis formed in a coronary artery affects a resistance of microvascular bed in a hyperemia state. Considering the experimental result of Non-Patent Document 2, it can be said that the subject-specific microvascular bed resistance should be determined by reflecting the blood flow state affected by a stenosis lesion formed in the subject-specific blood vessel. Therefore, in order to perform a CFD-LPM-associated hemodynamic simulation, which is more consistent with the physiological phenomena of a human body, the parameters of the LPM model that takes into account a subject-specific blood vessel shape should be obtained and used for the hemodynamic simulation.

FIG. 4 is a schematic diagram of a microvascular bed showing a modeling thereof. As shown in FIG. 4, the microvascular bed is composed of arterioles, capillaries and venules. The microvascular bed is difficult to segment because the diameter of the blood vessel thereof is very small. Therefore, in order to analyze the blood flow in the microvascular bed, a method of modeling the hemodynamic characteristics of the microvascular bed into an electric circuit and analyzing the electric circuit has been widely used. This analysis method is called a lumped parameter model (LPM) method. As shown in FIG. 4, the microvascular bed may be modeled into resistance R and compliance C. The microvascular bed is characterized by easily contracting and expanding depending on the internal pressure of the blood vessel, the metabolites (carbon dioxide, etc.) and the state of the autonomic nervous system. When the blood vessel in the microvascular bed contracts and expands, the blood vessel diameter is changed. The blood flow resistance is changed according to the change in the blood vessel diameter. The blood flow rate is changed according to the change in the blood flow resistance.

For example, it is assumed that the microvascular bed shown in FIG. 4 is connected to a stenosed branch of a coronary artery. If there is a lesion such as a stenosis or the like in the coronary artery under a hyperemia state, the pressure Pd (distal pressure) in the distal coronary artery on the downstream side of the lesion becomes lower than the pressure Pa (aortic pressure) in the proximal coronary artery on the upstream side of the lesion. When the pressure (Pd) applied to the microvascular bed becomes low, the diameter of the microvascular bed decreases. When the diameter of the microvascular bed becomes small, the blood flow resistance (Rm) of the microvascular bed increases. Therefore, the blood flow rate (Qd) in the microvascular bed is also reduced. Conversely, when there is no lesion such as a stenosis or the like in the coronary artery so that the pressure (Pd) applied to the microvascular bed does not decrease, the diameter of the microvascular bed is not reduced and the blood flow rate (Qd) is not decreased. After all, it is physiologically reasonable to assume that the hemodynamic characteristics of the microvascular bed are determined by the blood flow rate (Q0) in the microvascular bed and the pressure (P0) applied to the microvascular bed. In conclusion, the parameters of the LPM model representing the hemodynamic characteristics of the microvascular bed need to be determined by reflecting the pressure (Pd) applied to the microvascular bed and the blood flow rate (Qd) of the blood supplied to the microvascular bed, which depend on the shape of the blood vessel associated with the microvascular bed. In addition, this conclusion is not limited to the coronary artery of the heart, but is applicable to microvascular beds connected to all blood vessels of the human body including a cerebral blood vessel.

SUMMARY

A first object of the present invention is to provide a novel CFD-LPM-coupled blood flow simulation method and apparatus for a subject-specific three-dimensional blood vessel model. The new blood flow simulation method and apparatus is a method and apparatus in which parameters of an LPM model are obtained by reflecting the shape of a three-dimensional blood vessel model and a CFD-LPM-coupled blood flow simulation is performed by applying the parameters A second object of the present invention is to provide a method and apparatus for estimating hemodynamic characteristics of a microvascular bed connected to a subject-specific blood vessel, i.e., resistance and compliance, through the use of the novel CFD-LPM-coupled blood flow simulation method and apparatus.

According to one aspect of the present invention, there is provided a blood flow simulation method for a subject-specific three-dimensional blood vessel model using a computer system. The simulation method according to the present invention includes: (a) receiving the subject-specific three-dimensional blood vessel model; (b) generating a CFD model (analysis model) for blood flow analysis by applying a blood flow equation to the subject-specific three-dimensional blood vessel model; (c) setting an initial condition and a boundary condition in the CFD model; (d) generating an LPM model (lumped parameter model) including artery parameters and microvascular bed parameters to provide an outlet boundary condition of the CFD model; and (e) performing a blood flow simulation for the CFD model by coupling the CFD model and the LPM model, wherein the act of (e) performing the blood flow simulation for the CFD model by coupling the CFD model and the LPM model includes: (f) performing a blood flow simulation for the CFD model under the initial condition and the boundary condition; (g) calculating a blood flow rate Qi and a total outflow blood flow rate Qtot_cfd for each outlet of the CFD model by the blood flow simulation; (h) updating the microvascular bed parameters of the LPM model by using the blood flow rate for each outlet and the total outflow blood flow rate of the CFD model; (i) updating the boundary condition of the outlet of each branch of the CFD model by using the updated LPM model; and (j) repeatedly performing the acts of (f) to (i) until a convergence condition of the blood flow simulation for the CFD model is satisfied.

In some embodiments, the artery parameters and the microvascular bed parameters of the LPM model may be connected in series, the artery parameters may include an artery resistance Ra and an artery compliance Ca connected in parallel, and the microvascular bed parameters may include a microvascular bed resistance Rm and a microvascular bed compliance Cm connected in parallel.

In some embodiments, the artery parameters may have parameter values determined by using a length of a branch of the subject-specific three-dimensional blood vessel model.

In some embodiments, the artery parameters may have parameter values determined by using a diameter of a branch end of the subject-specific three-dimensional blood vessel model.

In some embodiments, the artery parameters may be parameter values determined by a CFD-LPM-coupled simulation for the subject-specific three-dimensional blood vessel model. In this case, the LPM model used in the CFD-LPM-coupled simulation for determining the artery parameters may be an LPM model including only the artery parameters. A pressure condition in a resting state of a subject may be used as a pressure condition downstream of the artery parameters of the LPM model in the CFD-LPM-coupled simulation.

In some embodiments, in the act of (h) updating the microvascular bed parameters of the LPM model by using the blood flow rate for each outlet of the CFD model and the total outflow blood flow rate of the CFD model, a microvascular bed compliance parameter $C_{m,i}$ of the LPM model is updated by a value obtained using Equation 12 described in the Detailed Description. The microvascular bed resistance parameter $R_{m,i}$ of each branch may be updated to a value obtained using Equation 10 and Equation 7 of the Detailed Description. Equation 12 approximates a value obtained by dividing an outflow blood flow rate $Q_i$ of an outlet of each branch obtained through a CFD model simulation by a difference between a systolic blood pressure and a diastolic blood pressure measured from a subject and multiplying the outflow blood flow rate $Q_i$ by a heart rate cycle. Equation 10 is an equation for obtaining the resistance $R_{m,ref}$ of the selected reference branch, and Equation 7 is an equation that imparts a constraint that the product of the microvascular bed resistance $R_{m,i}$ and the microvascular bed compliance $C_{m,i}$ is the time constant.

In some embodiments, in the act of (i) updating the boundary condition of the outlet of each branch of the CFD model by using the updated LPM model, the blood pressure set as the boundary condition of the outlet of each branch of the CFD model may be a blood pressure obtained using Equation 15 described in the Detailed Description.

According to another aspect of the present invention, there is provided a blood flow simulation apparatus for a subject-specific three-dimensional blood vessel model. The apparatus According to the present invention includes: a processor; and a memory in which a computer program to be executed in the processor is stored. The computer program is configured to perform: (a) receiving the subject-specific three-dimensional blood vessel model; (b) generating a CFD model (analysis model) for blood flow analysis by applying a blood flow equation to the subject-specific three-dimensional blood vessel model; (c) setting an initial condition and a boundary condition in the CFD model; (d) generating an LPM model (lumped parameter model) including artery parameters and microvascular bed parameters to provide an outlet boundary condition of the CFD model; and (e) performing a blood flow simulation for the CFD model by coupling the CFD model and the LPM model. The act of (e) performing the blood flow simulation for the CFD model by coupling the CFD model and the LPM model includes: (f) performing a blood flow simulation for the CFD model under the initial condition and the boundary condition; (g) calculating a blood flow rate Qi and a total outflow blood flow rate Qtot_cfd for each outlet of the CFD model by the blood flow simulation; (h) updating the microvascular bed parameters of the LPM model by using the blood flow rate for each outlet and the total outflow blood flow rate of the CFD model; (i) updating the boundary condition of the outlet of each branch of the CFD model by using the updated LPM model; and (j) repeatedly performing the acts of (f) to (i) to calculate at least one hemodynamic physical quantity until a convergence condition of the blood flow simulation for the CFD model is satisfied.

The parameters of the LPM model obtained by the conventional method fail to reflect the effect of the parameter value according to the change in the shape of the blood vessel when there is a lesion such as a stenosis or the like in the blood vessel. In addition, according to the conventional method, it is difficult to perform complicated calculations or invasive measurements in order to obtain the LPM parameters. Moreover, there is a problem that the accuracy of the blood flow simulation performed with incorrect LPM parameters is low.

According to the CFD-LPM-coupled simulation method for the subject-specific three-dimensional blood vessel model according to the present invention, it is possible to easily obtain the microvascular bed parameters of the LPM model that reflects the shape of the blood vessel. In addition, it is possible to perform a more accurate blood flow simulation for a subject-specific blood vessel by using the microvascular bed parameters of the LPM model that reflects the change in the shape of the blood vessel.

By performing the blood flow simulation for the three-dimensional vessel model of the subject-specific blood vessel, it is possible to calculate hemodynamic quantities of interest for the subject-specific blood vessel. The hemodynamic quantities of interest include, for example, a coronary artery fractional flow reserve (FFR), a coronary flow reserve (CFR), an index of microvascular resistance (IMR), an instantaneous wave-free ratio (IFR), a basal stenosis resistance, a hyperemic stenosis resistance, and the like.

DETAILED DESCRIPTION

Hereinafter, preferred embodiments of the present invention will be described with reference to the accompanying drawings. The embodiments described herein are directed to a subject-specific three-dimensional coronary artery model. The CFD-LPM-coupled blood flow simulation method and apparatus described below is exemplary and is not limited to a three-dimensional coronary artery model. The CFD-LPM-coupled blood flow simulation method and apparatus according to the present invention may be applied to any three-dimensional blood vessel model for human organs, such as a three-dimensional cerebrovascular model and the like.

In addition, the embodiments described in the subject specification are intended to aid visual understanding in order to describe the method according to the present invention. The digital image is a digital representation of an object such as a blood vessel or the like, and the processing on the digital image is described as identifying and manipulating the object. This processing of digital data is a virtual process stored in a memory of a computer system and performed by a processor. That is, it is to be understood that the method according to the present invention is stored in a memory of a computer system and is performed by a processor of a computer system.

Figure 5:
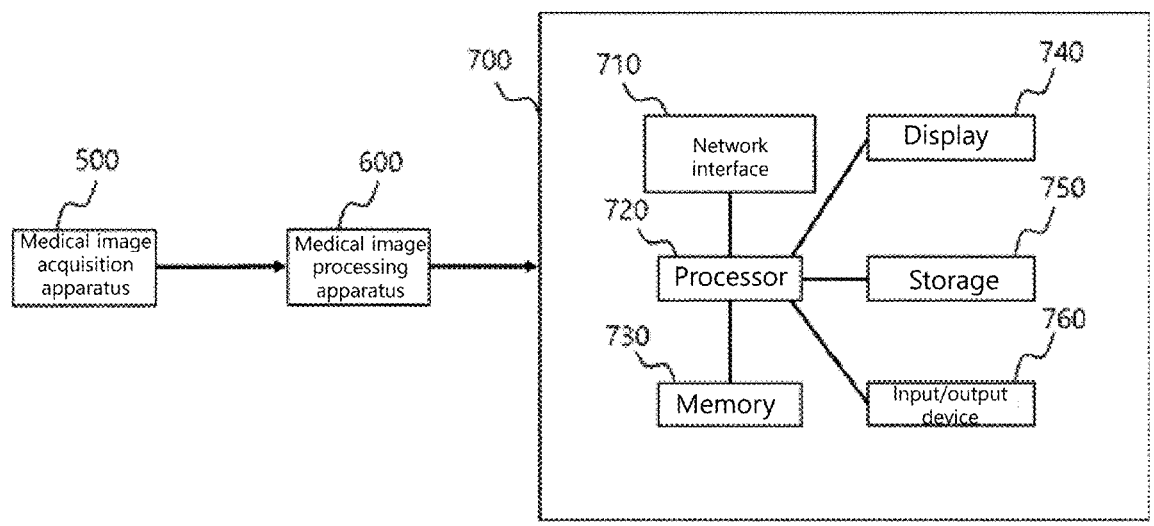
FIG. 5 is a schematic diagram of an apparatus according to the present invention.

CFD-LPM-Coupled Blood Flow Simulation Apparatus According to the Present Invention FIG. 5 is a schematic diagram of a blood flow simulation apparatus for a subject-specific three-dimensional blood vessel model according to the present invention. The apparatus 700 according to the present invention may be configured as a typical computer system. The computer system includes a processor 720 and a memory 730. The processor 720 executes computer program instructions stored in the memory 730 to perform a blood flow simulation for a subject-specific three-dimensional blood vessel model according to the present invention. In addition, the apparatus 700 may include a storage 750 for storing data, a display 740 for displaying simulation results, an input/output device 760 for inputting or outputting data, and a network interface 710. A medical image acquisition apparatus 500 provides medical image data for generating a subject-specific three-dimensional blood vessel model. The medical image acquisition apparatus 500 is an apparatus for capturing three-dimensional image data of a human body, such as a CT (CCTA), MRI (MRA), an ultrasound imaging apparatus, or the like. A medical image processing apparatus 600 is an apparatus that processes (segments) the medical image data provided from the medical image acquisition apparatus 500 to model a three-dimensional shape in a region of interest. The medical image processing apparatus 600 may be a separate computer system or a computer program to be executed in the apparatus 700.

The memory 730 of the CFD-LPM blood flow simulation apparatus according to the present invention stores a computer program in which the method according to claim 1 of the present invention is written in a program language. The apparatus 700 according to the present invention causes the processor 720 to execute the computer program to perform the blood flow simulation according to the method recited in the claims.

Generation of Subject-Specific Three-Dimensional Blood Vessel Model

Figure 4:
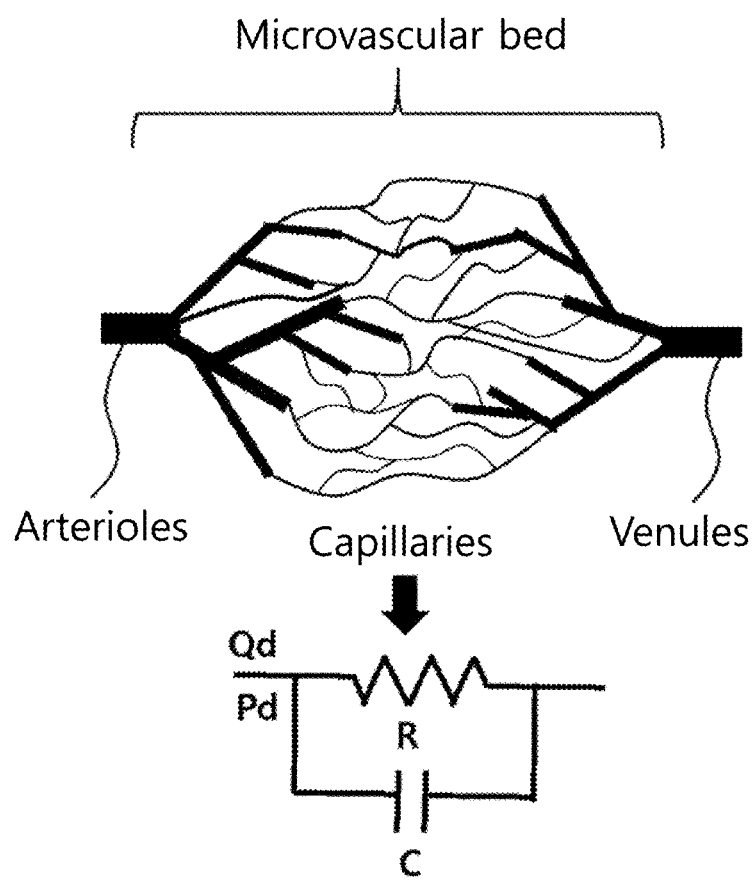
FIG. 4 is a schematic diagram of a microvascular bed.

In the major organs of the human body such as the heart or the brain, blood vessels are distributed throughout the organ to supply blood to the cells that make up the organs. The blood supplied from the heart circulates back to the heart through arteries, arterioles, capillaries, venules and veins. A microvascular bed is composed of arterioles, capillaries and venules. FIG. 4 schematically illustrates a microvascular bed and an LPM model for the microvascular bed. The average blood vessel diameter of arterioles is about 30 μm, the average vessel diameter of venules is about 20 μm, and the average diameter of capillaries is about 8 μm.

Figure 6:
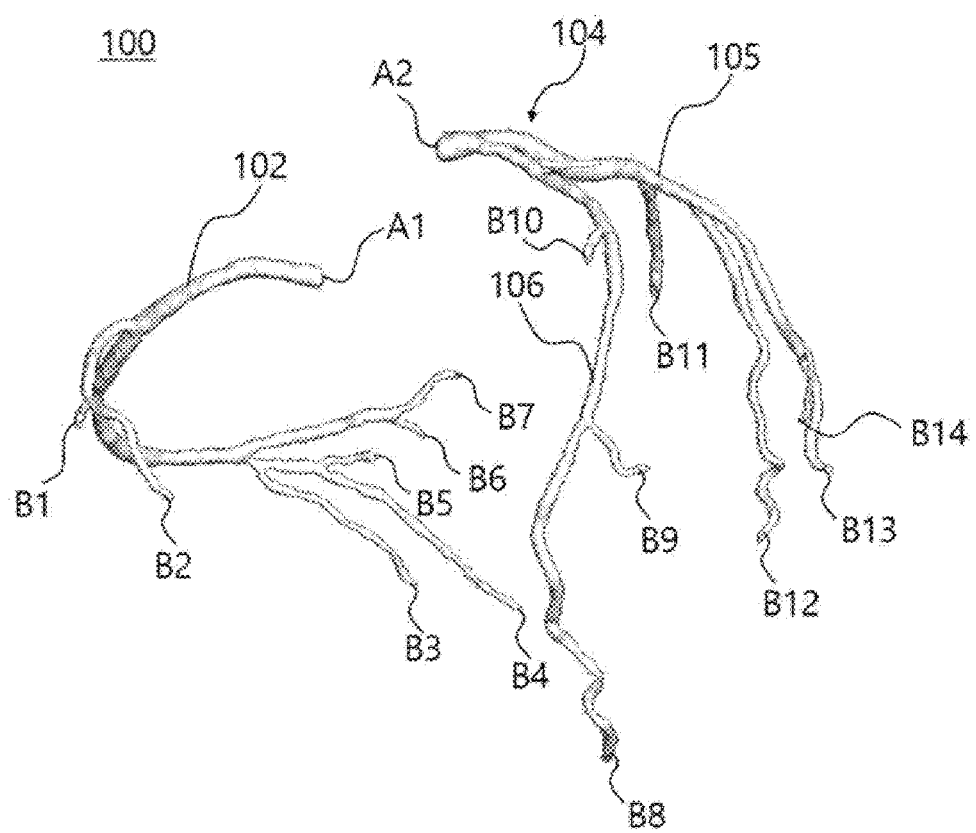
FIG. 6 is a diagram showing a three-dimensional coronary artery model to which the method according to the present invention is applied.

FIG. 6 shows an example of a three-dimensional blood vessel model for a coronary artery of a heart. The three-dimensional coronary artery model 100 shown in FIG. 6 is the result of automatic segmentation of a subject-specific coronary artery by applying the algorithm disclosed in Patent Document 1 to the cardiac CT image data (CCTA image data) provided from the medical image acquisition apparatus 500.

The three-dimensional coronary artery model 100 is divided into a right coronary artery 102 (RCA) and a left coronary artery 104. In addition, the left coronary artery 104 is divided into a left circumflex coronary artery (LCX) 105 and a left anterior descending coronary artery (LAD) 106. The three-dimensional coronary artery model 100 is composed of two inlets A1 and A2 connected to the aorta, a plurality of outlets B1 to B14, and tree-shaped blood vessels that connect the inlets and outlets. Although the downstream portion of each of the outlets B1 to B14 of the coronary artery 100 is not segmented from the CT image data due to technical difficulties, it is connected to the microvascular bed through small-diameter blood vessels connected to the respective outlets. Segmentation techniques for obtaining a three-dimensional blood vessel model from three-dimensional medical image data, which are known so far, are difficult to accurately segment a blood vessel having a diameter of 1 mm or less. The three-dimensional coronary artery model 100 of the present embodiment is a three-dimensional, blood vessel model having a diameter of about 1 mm or more.

Figure 1:
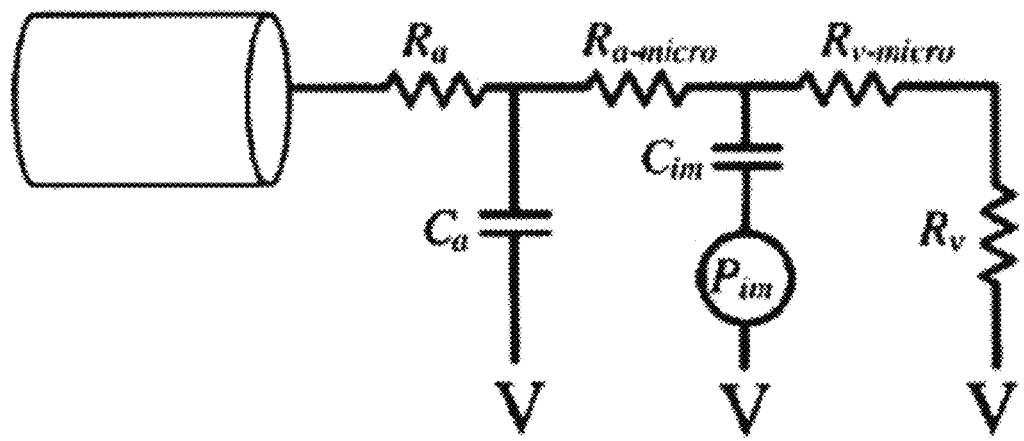
FIG. 1 is a schematic diagram showing a lumped parameter coronary artery microvascular bed model linked to an outlet of a coronary artery, which is disclosed in Non-Patent Document 1.
Figure 2:
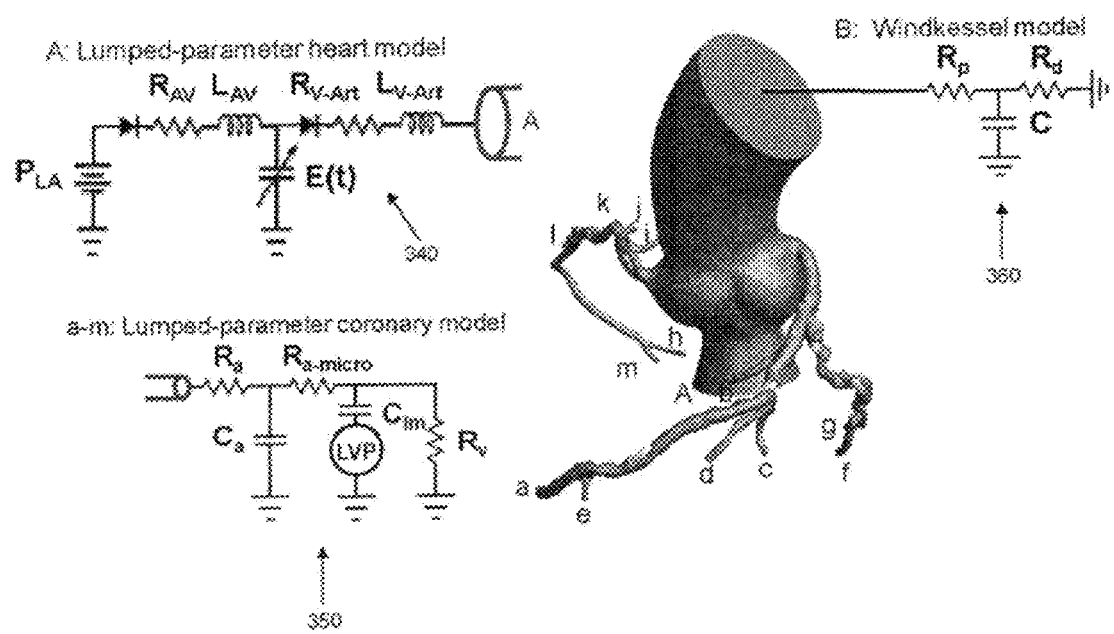
FIG. 2 is a conceptual diagram of a blood flow simulation model (CFD-LPM-coupled simulation model) of a coronary artery, which is disclosed in Patent Document 3.
Figure 3:
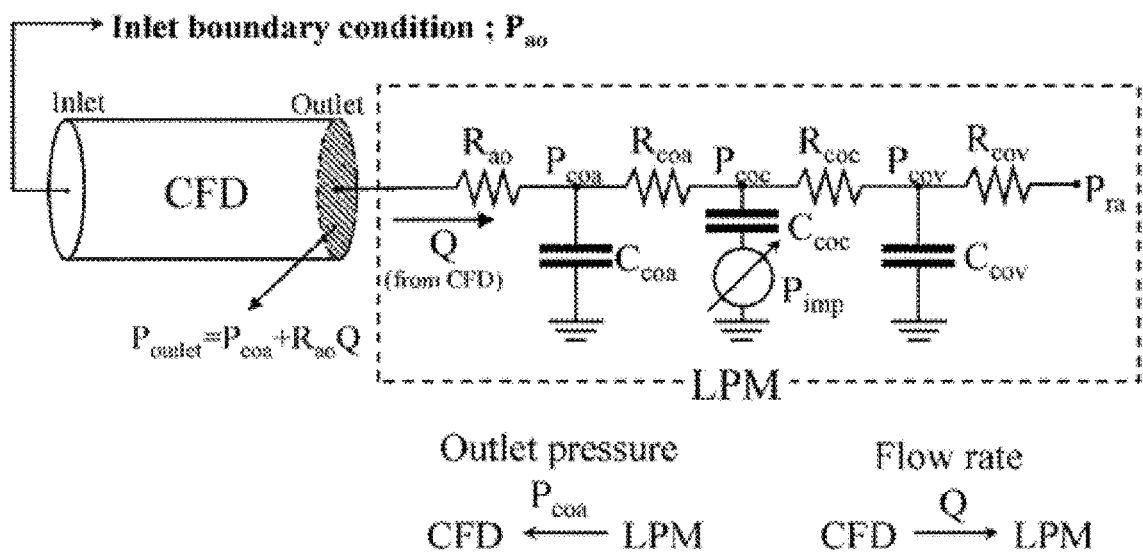
FIG. 3 is a schematic diagram showing a method of performing a blood flow simulation of a coronary artery by coupling a CFD model and an LPM model, which is disclosed in Patent Document 4.

CFD-LPM-Coupled Simulation Method for Conventional Three-Dimensional Blood Vessel Model One of the conventional methods of performing a blood flow simulation for the three-dimensional coronary artery model 100 as shown in FIG. 6 is disclosed in Patent Document 4. FIG. 3 schematically shows the method disclosed in Patent Document 4. Referring to FIG. 3, the boundary condition for each outlet of the three-dimensional blood vessel model 100 is provided in association with the LPM model to perform a blood flow simulation for the three-dimensional CFD model.

Figure 7:
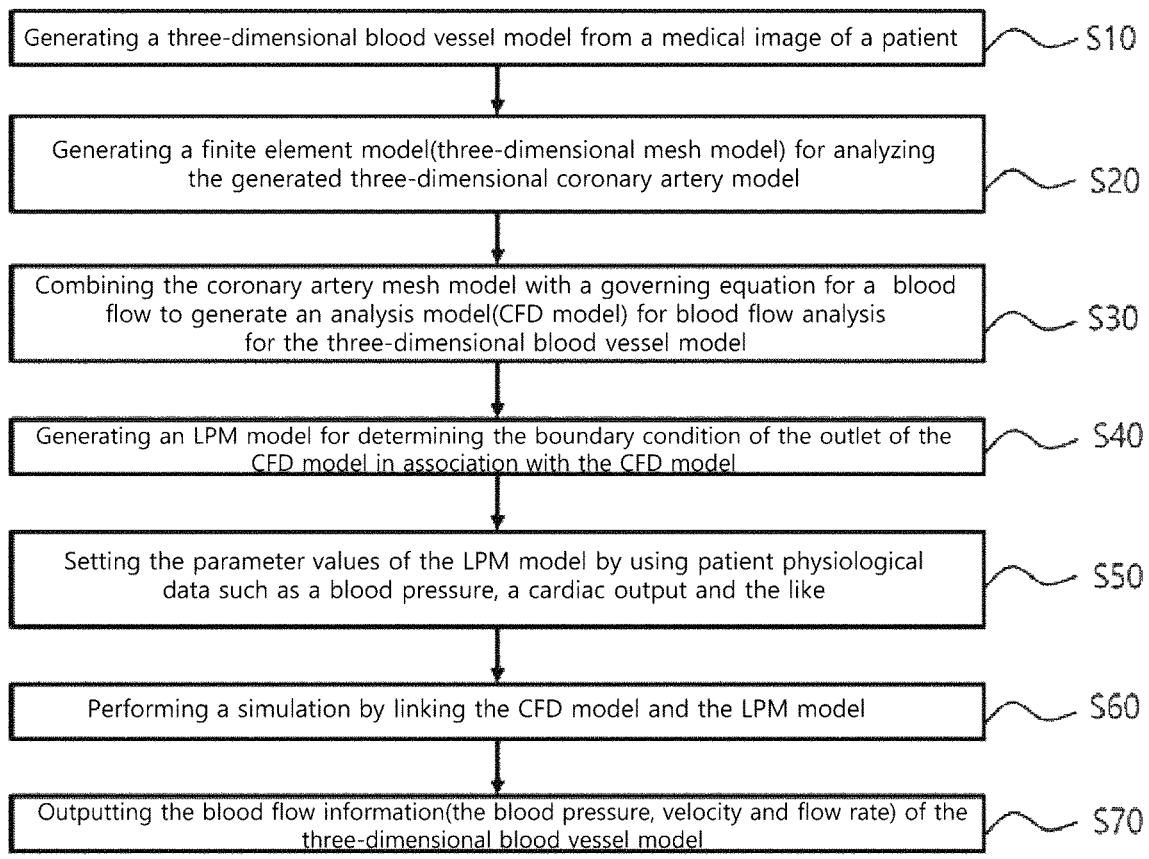
FIG. 7 is a flowchart for explaining a conventional CFD-LPM-coupled simulation method.

FIG. 7 is a flowchart of a conventional CFD-LPM-coupled blood flow simulation method for a three-dimensional coronary artery model 100. First, a three-dimensional coronary artery model 100 is generated by receiving medical image data of a patient through the use of a computer system (S10). As the medical image data, CCTA data is used when analyzing the coronary artery of the heart. MRI data may be used when analyzing cerebral blood vessels.

Figure 8:
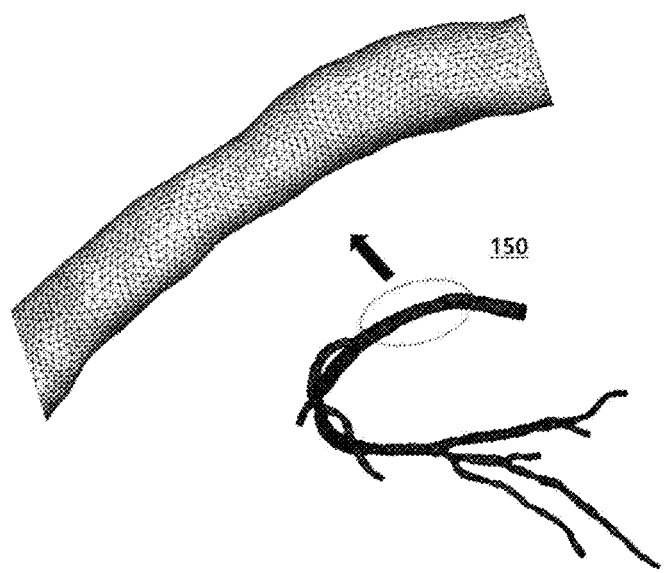
FIG. 8 is a schematic diagram of a three-dimensional mesh model of a coronary artery.

Next, a finite element model (three-dimensional mesh model) for analyzing the generated three-dimensional coronary artery model 100 is generated (S20). FIG. 8 illustrates a part of the three-dimensional coronary artery mesh model 150 generated by processing the three-dimensional coronary artery model 100. A method of generating a finite element mesh model for a three-dimensional shape model is well-known in the field of a CFD simulation. Therefore, the detailed description thereof will be omitted.

Next, the coronary artery mesh model 150 is combined with a governing equation for a blood flow to generate an analysis model (CFD model) for blood flow analysis for the three-dimensional blood vessel model (S30). As the governing equation for a blood flow in a blood vessel, the Navier-Stokes equation and the continuity equation for a blood flow are applied. The CFD model is constructed in the form of a large-scale matrix equation, which represents the physical relationship between finite element meshes, by applying the governing equation to each mesh that constitutes the three-dimensional mesh model. In order to analyze the analysis model, it is necessary to determine the boundary conditions of the inlet and outlet of the analysis model.

Next, an LPM model for determining the boundary condition of the outlet of the CFD model is generated in association with the CFD model (S40). The LPM model is a model for determining the pressure at the inlet and outlet of the CFD model or the flow rate (or the blood flow velocity) of the blood flowing into the inlet or flowing from the outlet. The LPM model represents the blood flow characteristics of the microvascular bed LPM model are determined according to the resistance by simplifying the blood flow characteristics into a resistance and a capacitance. The blood flow characteristics of the LPM model are determined according to the resistance and capacitance values (resistance/capacitance parameter values) constituting the LPM model.

The simulation method disclosed in Patent Document 4 sets the parameter values of the LPM model by non-invasively measuring patient physiological characteristics such as a blood pressure, a cardiac output, a blood vessel length and the like (S50). The simulation method disclosed in Patent Document 3 sets the parameter values of the LPM model by non-invasively measuring patient physiological characteristics such as a blood pressure, a cardiac output, a myocardial mass and the like. The measured blood pressure (Pao) is set as the boundary condition at the inlet of the CFD model. The LPM model used in the conventional simulation method is the LPM model shown in FIG. 3.

After the parameter values of the LPM model shown in FIG. 3 are set, as shown in FIG. 3, a simulation is performed by coupling the CFD model and the LPM model (S60). The blood flow simulation results for the CFD model, for example, the blood pressure, velocity and flow rate of the blood flowing inside the three-dimensional blood vessel model in a steady state, are outputted (S70).

The conventional CFD-LPM-coupled blood flow simulation method for the three-dimensional blood vessel model as described above determines the boundary conditions of the CFD model by using the parameters of the LPM model in which the shape of the three-dimensional blood vessel model is not taken into account. Therefore, there is a problem that the conventional CFD-LPM-coupled blood flow simulation method fails to accurately reflect physiological phenomena.

Novel CFD-LPM-Coupled Simulation Method for Three-Dimensional Blood Vessel Model According to the Present Invention The hemodynamic characteristics of the microvascular bed, i.e. the resistance and the compliance, are determined by the pressure and flow rate of the blood flow passing through the microvascular bed, and the blood flow rate in the microvascular bed is affected by the stenosis lesion formed inside the blood vessel. The novel CFD-LPM-coupled simulation method according to the present invention is a simulation method that reflects such physiological phenomena. The CFD-LPM-coupled simulation method according to the present invention is a method of obtaining parameters of an LPM model corresponding to a microvascular bed suitable for the state of a blood flow passing through the microvascular bed when performing a hemodynamic simulation, and applying the parameters to the simulation.

Figure 9:
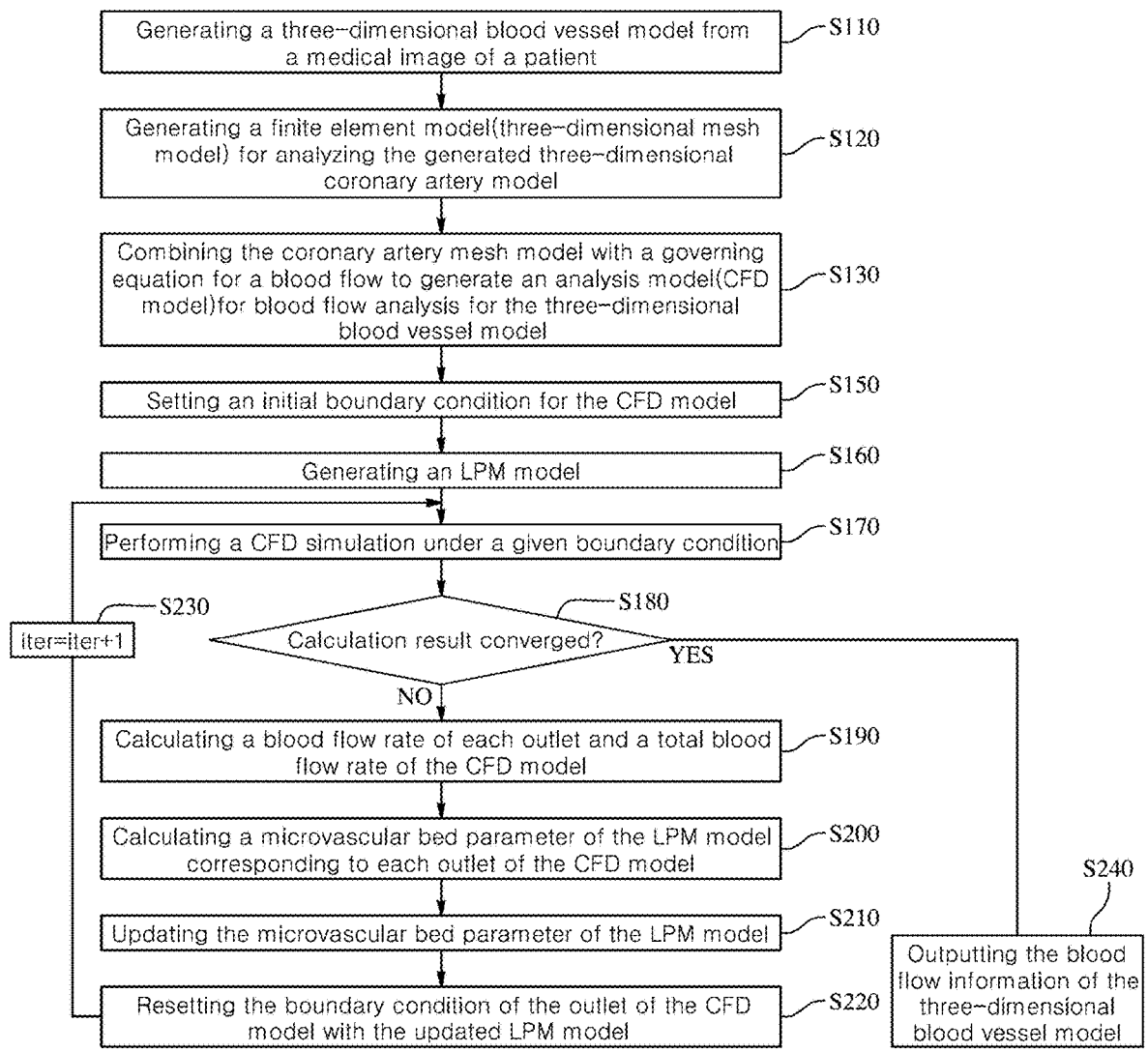
FIG. 9 is a flowchart for explaining a novel CFD-LPM-coupled blood flow simulation method according to the present invention.

FIG. 9 is a flowchart illustrating a novel CFD-LPM-coupled simulation method according to the present invention. In order to apply the CFD-LPM-coupled blood flow simulation method according to the present invention, it is assumed that the blood vessel system of a specific organ to be simulated satisfies the following four physiological principles.

(Assumption 1)

The total resistance of a blood vessel system of a particular organ is the sum of the parallel distributions of resistance of the branched blood vessels that make up the blood vessel system. In addition, the total resistance of the blood vessel system is determined by the relationship between a blood pressure and a blood flow rate of the blood estimated to flow through the blood vessel system.

(Assumption 2)

In the LPM model to be liked to each branch of the blood vessel system, artery parameters and microvascular bed parameters are connected in series. The artery parameters include artery resistance (Ra) and arterial compliance (Ca), and the microvascular bed parameters include microvascular bed resistance (Rm) and microvascular bed compliance (Cm). The number added after each parameter indicates the number of the branch to which the parameters are linked.

(Assumption 3)

In the LPM model connected to each branch of the blood vessel system, the product of the microvascular bed resistance (Rm) and the microvascular bed compliance (Cm) has a constant value as a time constant.

The blood flow in each branch of the blood vessel of the blood vessel system is driven by the ejection pressure applied to the blood ejected from the left ventricle by the heartbeat. Therefore, even though there is a difference in the flow rate of the blood flowing through each branch of the blood vessel system, the cycle of the blood flow supplied to the microvascular bed through each branch and the cycle of the blood flow discharged to the vein through the microvascular bed need to be approximately the same as the cycle of the heartbeat (or the cycle of the ejection pressure applied to the blood). That is, only when the time constants, one of the characteristics of the blood flow in each microvascular bed, are approximately the same, the continuous equation for the blood flow in the branches of the blood vessel system, the microvascular bed and the vein in time will be satisfied.

On the other hand, the oxygen demand of a specific organ and the supply of oxygen to a blood vessel need to be balanced. Therefore, the blood supplied from the aorta to the arterial blood vessel system of a specific organ reaches the terminal tissues at the same time in each branch and exchanges oxygen with the terminal tissues. Thereafter, the blood is recovered to the venous system. In fact, it is reported that the time for the oxygen-saturated blood entering the cardiovascular system to reach the tissues is almost the same (Non-Patent Document 3). In the absence of very serious arterial lesions, this assumption is valid from a physiological view point. This phenomenon has been similarly observed in the lungs (Non-Patent Document 4). In addition, the product of artery resistance (Ra) and arterial compliance (Ca) of the LPM model will also have an almost constant value as a time constant.

(Assumption 4)

Figure 10:
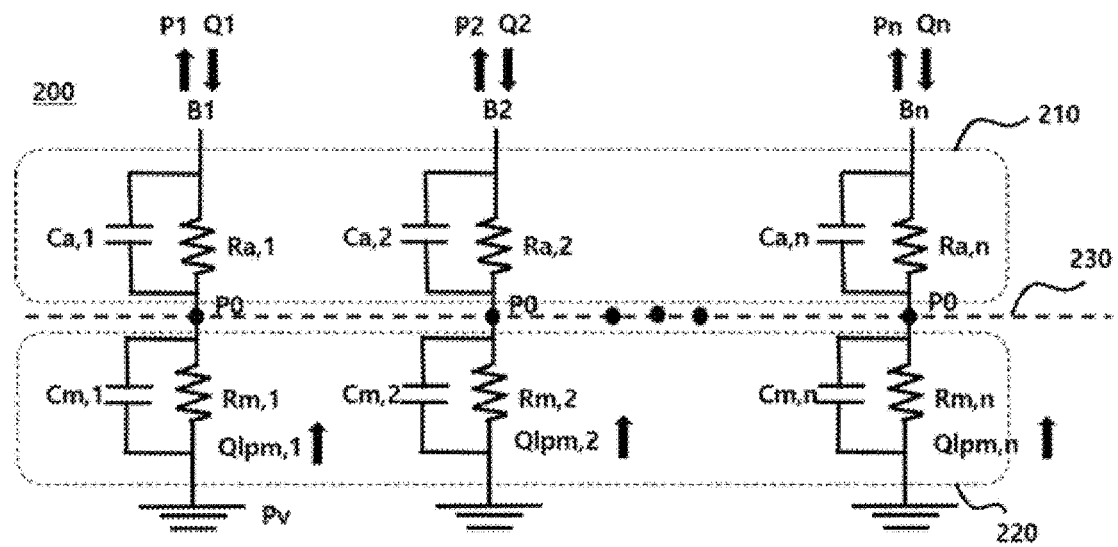
FIG. 10 is a schematic diagram of an example of an LPM model applied to the novel CFD-LPM-coupled simulation method according to the present invention.
Figure 16:
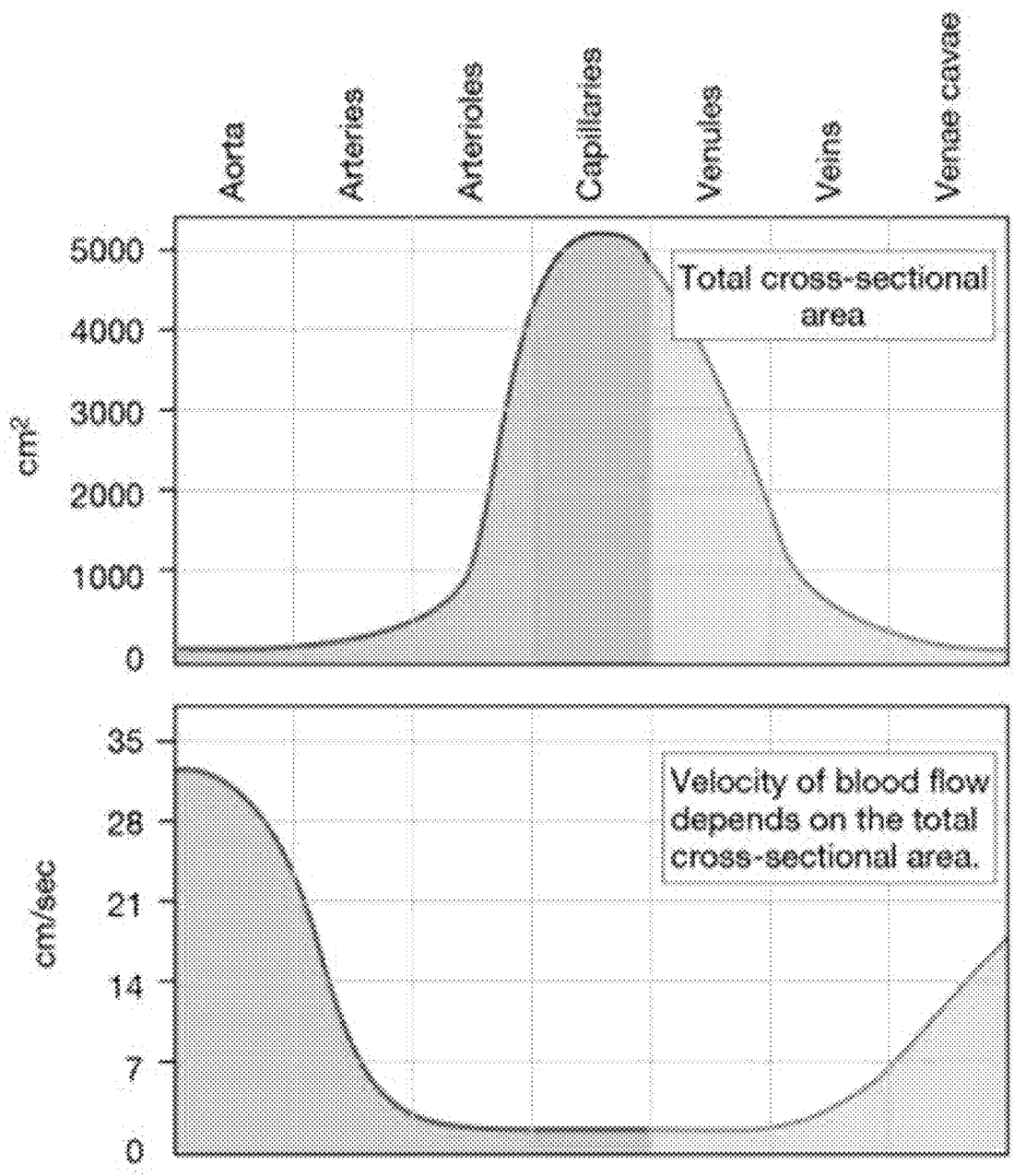
FIG. 16 is a graph showing blood flow velocities and blood vessel cross-sectional areas for respective blood circulation vessels.

In the LPM model shown in FIG. 10, the blood pressure P0 between the artery parameter and the microvascular bed parameter linked to each branch remains the same regardless of the flow rate of the blood flowing through each branch. In other words, it is assumed that the blood pressures on the upstream side of the microvascular beds connected to the respective branches of the blood vessel system remain the same. This assumption can be inferred from the graph that shows the blood flow velocity for each blood vessel and the blood vessel cross-sectional area, which is shown in FIG. 16. As shown in FIG. 16, the velocity of the blood flow in the capillaries is constant. In addition, the average diameter of the capillaries is as constant as about 8 Therefore, the difference in blood pressure between the upstream side and the downstream side of the capillaries will be kept constant. The downstream ends of the capillaries are connected to the vein, and the blood pressure in the vein has an almost constant value. Therefore, it can be said that the blood pressure on the upstream side of the capillaries is also constant. In addition, since most of the resistance of the microvascular bed is due to capillaries, it can be assumed that the same blood pressure P0 acts on upstream side of the branches of the blood vessel system near the microvascular bed.

Method of Calculating Microvascular Bed Parameter of LPM Model that Satisfies the Above Assumption Assuming the above four assumptions for the arterial blood vessels constituting the respective branches of a blood vessel system of a specific organ and the microvascular beds on the downstream side thereof, it is possible to derive the relational equations that bind the parameters of the LPM model to be linked to the respective branches.

Prior to deriving the relational equations, it is assumed that the theoretical blood flow rate of the blood entering the artery of a specific organ is given in advance according to the state of a subject. For example, when a blood flow simulation is performed on a subject in a resting state, it can be assumed that about 4% of the blood of the cardiac output (CO) of the coronary artery of the heart flows into the coronary artery system. In addition, when simulating the coronary artery fractional flow reserve (FFR), which is an important indicator in the clinical practice of coronary artery patients, a blood flow simulation is performed in a state in which the microvascular bed is expanded by administering adenosine to a patient. Therefore, it can be assumed that the blood of a blood flow of about 4.5 times as large as the coronary artery blood flow rate flows into the coronary artery system (Non-Patent Document 5). In addition, when performing a blood flow simulation for a cerebral blood flow, it can be assumed that the blood of about 15% of the cardiac output (CO) in the resting state flows into the cerebrovascular system.

These blood flow inflow conditions that assume a specific state of a subject are widely used in the conventional FFR simulations and brain blood flow analysis techniques. In the present invention, the estimated blood flow rate that assumes a specific state of a subject is used to estimate the parameters of the LPM model linked to the outlet boundary condition of the CFD model in order to perform a simulation on a three-dimensional blood vessel model. In the subject specification, this estimated blood flow rate is referred to as 'theoretical blood flow rate'. If the actual flow resistance of the three-dimensional blood vessel model converges to almost zero, the theoretical blood flow rate will be close to the actual blood flow rate. In addition, the blood pressure data measured directly from the subject is applied to the boundary condition at the inlet of the three-dimensional blood vessel model (Non-Patent Document 6). Moreover, in this example, it is assumed that the blood flow in the CFD model and the LPM model is in a steady state.

FIG. 10 shows an example of an LPM model 200 to be linked to each outlet of the three-dimensional coronary artery model shown in FIG. 6 when applying the novel CFD-LPM-coupled blood flow simulation method according to the present invention. The LPM model 200 of this example is virtually connected to each of the branches B1 to B14 of the three-dimensional coronary artery model 100 shown in FIG. 6. In the LPM model to be linked to each branch of the three-dimensional coronary artery model 100, artery parameters 210 and microvascular bed parameters 220 are connected in series. The artery parameters 210 are composed of artery resistance (Ra) and artery compliance (Ca) connected in parallel, and the microvascular bed parameters 220 are composed of microvascular bed resistance (Rm) and microvascular bed compliance (Cm) connected in parallel (Assumption 2). In FIG. 9, the numbers indicated after the respective parameters Ra, Ca, Rm and Cm of the LPM model 200 indicate the numbers of the associated branches of the three-dimensional coronary artery model 100. For example, the artery resistance of the LPM model connected to branch 1 is Ra,1, the artery compliance is Ca,1, the microvascular bed resistance is Rm,1, and the microvascular bed compliance is Cm, 1. In addition, when the simulation is performed by coupling the CFD model and the LPM model, Q1 is the blood flow rate of the blood flowing out from the outlet of branch 1 in the CFD model, and P1 is the boundary condition to be set for the outlet of branch 1 of the CFD model. The blood flow rate Qi is obtained by performing a simulation for the CFD model, and the boundary condition P1 is obtained by performing a calculation for the LPM model. In addition, Pv is the pressure after the venules of the microvascular bed.

Referring to FIG. 10, the parameters of the LPM model to be linked to each branch of the three-dimensional coronary artery model shown in FIG. 6 are composed of Ra,i, Ca,i, Rm,i, and Cm,i, where i is the index of each of the branches. In addition, it is assumed that the theoretical blood flow rate of the blood flowing into the three-dimensional coronary artery model shown in FIG. 6 is Qtot. The theoretical blood flow rate refers to the maximum blood flow rate in the case of assuming that there is no resistance of the three-dimensional coronary artery model 100. It is known that when an ordinary healthy person is in a resting state, about 4% of the cardiac output (CO) is supplied to the coronary artery, and further that when hyperemia is induced by adenosine, the blood flow rate is about 4.5 times as large as the blood flow rate in a normal state. In the case of the cerebral artery, it is known that about 15% of the cardiac output is supplied to the cerebral artery in a normal state, and further that when the microvascular bed is expanded by carbon dioxide or a drug such as acetazolamide or the like, the blood of a flow rate about twice as much as the blood flow rate in the normal state is supplied to the cerebral artery (Non-Patent Document 7).

When the theoretical blood flow Qtot is assumed for the LPM model shown in FIG. 10, the total resistance Rtot can be obtained by the following Equation (1). In FIG. 10, the pressure Pv of the vein at the end of the LPM model is assumed to be 0 for the sake of convenience.

$$R_{tot} = \frac{P_{ao}}{Q_{tot}} \tag{1}$$

The total resistance Rtot is distributed in parallel to the resistances of the respective branches of the coronary artery system. Therefore, the total resistance Rtot and the resistance of each of the branches satisfy the relationships as shown in Equation 2 and Equation 3 below (Assumption 1).

$$R_i = R_{a,i} + R_{m,i} \tag{2}$$

$$\frac{1}{R_{tot}} = \sum_{i=1}^{n} \frac{1}{R_i} \tag{3}$$

In the above equations, subscript i is the number of each of the branches, and n is the total number of branches. In addition, Ri is the total resistance of the i-th branch, Ra,i is the artery resistance of the i-th branch, and Rm,i is the microvascular bed resistance of the i-th branch.

Further, under Assumption 4, the pressure on the downstream side of the artery resistance Ra,i of each branch of the LPM model shown in FIG. 10 is equal to P0. Therefore, the relationships as shown in Equation 4 and Equation 5 below are established. That is, the total resistance of the blood vessel system can be expressed as the sum of the total artery resistance and the total microvascular bed resistance.

$$R_{tot} = R_{a,tot} + R_{m,tot} \tag{4}$$

$$\frac{1}{R_{a,tot}} = \sum_{i=1}^{n} \frac{1}{R_{a,i}}, \frac{1}{R_{m,tot}} = \sum_{i=1}^{n} \frac{1}{R_{m,i}} \tag{5}$$

In the above equations, Ra,tot is the sum of the respective artery resistances, and Rm,tot is the sum of the microvascular bed resistances.

By reorganizing Equation 3, Equation 4 and Equation 5, the following Equation 6 can be obtained.

$$\frac{1}{R_{tot} - R_{a,tot}} = \frac{1}{R_{m,tot}} = \sum_{i=1}^{n} \frac{1}{R_{m,i}} \tag{6}$$

In addition, under Assumption 3, the relationship of Equation 7 is established between the microvascular bed resistance Rm and the microvascular bed compliance Cm.

$$R_{m,1}C_{m,1} = R_{m,2}C_{m,2} = \ldots = R_{m,n}C_{m,n} \tag{7}$$

If Equation 7 is reorganized by selecting, as a reference branch, the branch where the blood is expected to flow most in the boundary condition given when a simulation is performed on the CFD model, the following Equation 8 can be obtained.

$$R_{m,1} = \frac{C_{m,ref}}{C_{m,1}} R_{m,ref}, \, R_{m,2} = \frac{C_{m,ref}}{C_{m,2}} R_{m,ref}, \, \ldots, \, R_{m,n} = \frac{C_{m,ref}}{C_{m,n}} R_{m,ref} \quad (8)$$

In the above equation, subscript 'ref' means the microvascular bed resistance and compliance of the branch where the blood is expected to flow most. The reference branch is merely for the sake of convenience of explanation. It is not necessarily required that the branch determined as the reference branch in the actual calculation has the highest blood flow rate.

By substituting Equation 8 into Equation 6 and reorganizing Equation 6 for the reference branch, the following Equation 9 can be obtained.

$$\frac{1}{R_{tot} - R_{a,tot}} = \frac{1}{R_{m,ref}} \left( 1 + \frac{1}{R_{m,1}} + \ldots + \frac{1}{R_{m,n}} \right) = \frac{1}{R_{m,ref}} \left( 1 + \sum_{\substack{i=1 \\ i \neq ref}}^{n} \frac{C_{m,i}}{C_{m,ref}} \right) \quad (9)$$

When Equation 9 is reorganized for Rm,ref, it becomes Equation 10 below.

$$R_{m,ref} = (R_{tot} - R_{a,tot}) \left( 1 + \sum_{\substack{i=1 \\ i \neq ref}}^{n} \frac{C_{m,i}}{C_{m,ref}} \right) \quad (10)$$

If the value Rtot-Ra,tot and the ratio of the microvascular bed compliance Cm,i of other branches to the microvascular bed compliance Cm,ref of the reference branch for each branch are obtained from Equation 10, the microvascular bed resistance Rm,ref of the reference branch can be obtained.

Hereinafter, a method of obtaining a ratio Cm,i/Cm,ref of the microvascular bed compliance of other branches to the microvascular bed compliance of the reference branch when a CFD-LPM-coupled blood flow simulation is performed will be described.

The microvascular bed compliance Cm,i refers to the degree at which the blood can be stored in the microvascular bed. In addition, the microvascular bed compliance Cm,i is defined as a change in the volume of the microvascular bed with respect to a change in the pressure applied to the microvascular bed, and may be expressed as the following Equation 11.

$$C = \frac{dV}{dP} = \frac{dV/dt}{dP/dt} \quad (11)$$

In order to introduce the concept of flow rate in Equation 11, a change in pressure and volume is expressed with respect to a change in time. In the present invention, the definition of Equation 11 is approximated as shown in Equation 12 in order to obtain the microvascular bed compliance Cm,i for a branch of a specific blood vessel.

$$C_{m,i} = \left( \frac{dV/dt}{dP/dt} \right)_i \sim \frac{Q_i}{\Delta P_i / \Delta \tau} \quad (12)$$

In Equation 12, Qi is the blood flow rate in the i-th branch. Furthermore, ΔPi/Δτ represents the pressure change over time in the i-th branch.

In the present invention, if ΔPi is approximated by the pressure change during one cardiac cycle at each branch end, then Δτ becomes the cardiac cycle. If the blood flow simulation for a CFD model is performed under a given boundary condition and the blood flow rate Qi of the blood flowing out to each branch is obtained through the use of Equation 12, it is possible to obtain the microvascular bed compliance Cm,i for each branch of the LPM model. If the microvascular bed compliance Cm,i of each branch of the LPM model is obtained, the microvascular bed resistance Rm,ref of the reference branch can be obtained through the use of Equation 10. In addition, if the microvascular bed resistance Rm,ref of the reference branch is obtained, the microvascular bed resistance Rm,i and the microvascular bed compliance Cm,i of other branches can be obtained through the use of Equation 8.

Hereinafter, with reference to FIG. 9, a CFD-LPM-coupled blood flow simulation method according to the present invention will be described in detail using the relationship of the parameters of the LPM model described above. In the simulation according to the present invention, the microvascular bed parameters of the LPM model shown in FIG. 9, which are linked to each branch of the CFD model, are not set in advance, but are determined by a CFD-LPM-coupled simulation so as to conform to the shape of the CFD model. This example is directed to the blood flow simulation for the subject-specific coronary artery. However, this example is not limited thereto, and may be applied to any blood vessel system of a subject-specific organ such as cerebral blood vessel or the like.

First, a three-dimensional coronary artery model 100 is generated by receiving medical image data of a patient through the use of the computer system (S110). For medical imaging image data, CCTA data is used to interpret the coronary artery of the heart. MRI data may be used when analyzing cerebral blood vessels.

Next, a finite element model (three-dimensional mesh model) for analyzing the generated three-dimensional coronary artery model 100 is generated (S20). FIG. 8 illustrates a part of the three-dimensional coronary artery mesh model 150 generated by processing the three-dimensional coronary artery model 100. A method of generating a finite element mesh model for a three-dimensional shape model is well-known in the field of a CFD simulation. Therefore, the detailed description thereof will be omitted.

Next, the coronary artery mesh model 150 is combined with a governing equation for a blood flow to generate an analysis model (CFD model) for blood flow analysis for the three-dimensional blood vessel model (S30). As the analysis method for the CFD model, the PISO-type finite element method (FEM) used in Non-Patent Document 8 or Non-Patent Document 9 may be used. As the governing equation for a blood flow in a blood vessel, the Navier-Stokes equation and the continuity equation for a blood flow are applied. Assuming an incompressible viscous fluid, the governing equation for a blood flow is expressed by the Navier-Stokes equation as shown in Equation 13 and Equation 14 below.

$$\nabla \cdot \vec{u} = 0 \tag{13}$$

$$\rho \left\{ \frac{\partial \vec{u}}{\partial t} + (\vec{u} \cdot \nabla)\vec{u} \right\} = -\nabla p + \mu \nabla^2 \vec{u} \tag{14}$$

Equation 13 is a continuity equation for a fluid, and Equation 14 is a momentum conservation equation. In the above equations, $\rho$ is the density of a fluid, u is the velocity vector, t is the time, p is the pressure, and $\mu$ is the viscosity coefficient.

The FEM's Galerkin method is applied in order to combine the governing equation for a blood flow with the three-dimensional coronary mesh model 150 to discretize the governing equation into an analysis model (CFD model) for blood flow analysis. Finally, the governing equation is converted into algebraic equations at grid points. The algebraic equations are constructed in the form of large-scale matrix equations representing the physical relationship at the lattice points of the finite element mesh. By solving the algebraic equations at the grid points through the use of a computer, it is possible to obtain the blood flow velocities and the pressures at the grid points. The final results of the analysis for the CFD model appear as the velocities and the pressures at the grid points of the three-dimensional mesh model. In order to analyze the analysis model, the initial conditions at the grid points of the analysis model and the boundary conditions at an inlet and an outlet are determined (S150).

Next, an LPM model for determining the boundary condition of the outlet of the CFD model is generated in association with the CFD model (S160). The LPM model is a model for determining the pressures at the inlet and outlet of the CFD model or the flow rates (or the blood flow velocities) of the blood flowing into the inlet or flowing out from the outlet. The LPM model represents the blood flow characteristics of the microvascular bed in terms of resistance and compliance in a simplified manner. In addition, the blood flow characteristics of the LPM model are determined according to the resistance value and compliance value (resistance/compliance parameter values) constituting the LPM model. Among the parameters of the LPM model, the values of artery parameters Ra,i and Ca,i are first set. The values of the artery parameters Ra,i and Ca,i are values obtained in advance by a separate method. A method of obtaining the artery parameters Ra and Ca of the LPM model will be described later.

Next, a theoretical blood flow rate Qtot of the blood flowing into the coronary artery system in a specific state of the subject is set. The theoretical blood flow rate can be calculated by calculating the cardiac output (abbreviated as CO) using the heart rate and the stroke volume (abbreviated as SV) measured from a subject. In addition, using the ratio of the blood flow to the cardiac output flowing into a specific organ, which is known in the prior art documents, the blood flow rate of the blood flowing into a specific organ of a subject can be estimated and used as the theoretical blood flow rate Qtot. It is known that in a resting state, the ratio of the blood flow introduced into the heart is about 4% of the cardiac output, and the ratio of the blood flow introduced into the cerebral blood vessel is about 15% of the cardiac output (Non-Patent Document 10). In addition, when a blood flow simulation is performed for a hyperemic state which is the case of administering a vasodilator to a subject, the ratio of the blood flow in the hyperemic state known in the prior art documents may be used. It is known that when a subject is in a hyperemia state, the blood is introduced into the coronary artery at a blood flow rate of about 4.5 times as large as that in a resting period and the blood is introduced into the cerebral blood vessel at a flow rate of 2 to 32-3 times as large as that in a resting period (Non-Patent Document 10). After the theoretical blood flow rate Qtot of the subject is obtained, the total resistance Rtot of the coronary artery system is obtained according to Equation 1 using the arterial blood pressure Pao measured from the subject.

Next, a method of obtaining microvascular bed parameters Rm,i and Cm,i of the LPM model while performing a CFD-LPM-coupled simulation will be described. Before performing the CFD-LPM-coupled simulation, a reference branch is selected from a three-dimensional coronary artery model. For the sake of convenience, it may be possible to select a branch having a largest cross-sectional area and a largest length. This is because it is reasonable to estimate that a large amount of blood flows through a branch having a large cross-sectional area and a large length.

After the parameter values of the LPM model excluding the microvascular bed parameters are set and the boundary conditions of the CFD model are set, a simulation for the CFD model is first performed under the given boundary conditions (S170). In the first simulation for the CFD model, the blood pressure Pao measured from the subject is set as the inlet boundary condition of the CFD model, and the outlet boundary condition of each branch of the CFD model may be arbitrarily set. For the sake of convenience, a blood pressure of 50% or more of the measured blood pressure may be set as the boundary condition of each outlet.

Next, an outflow blood flow rate Qi of the blood that flows out to the outlet of each branch is obtained from the simulation results for the CFD model performed under the predetermined initial boundary conditions, and the sum of the outflow blood flow rates, i.e., the total outflow blood flow rate Qtot_cfd is obtained (S190). In this regard, i is the index of the branch.

Next, the microvascular bed parameters Rm,i and Cm,i of each branch are calculated using the outflow blood flow rate Qi of each outlet of the CFD model (S200). The order of calculating the microvascular bed parameters Rm,i and Cm,i is as follows. First, the blood flow rate Qi of the blood flowing out of each outlet of the CFD model is calculated, and the microvascular bed compliance Cm,i of each branch is obtained by applying the calculated result to Equation 12. Next, the resistance Rm,ref of the reference branch is calculated using the obtained microvascular bed compliance Cm,i of each branch and Equation 10, and the resistances Rm,i of the remaining microvascular beds are obtained using Equation 8.

Next, in order to provide an updated boundary condition for each branch of the CFD model, the microvascular bed parameters of the LPM model are updated using the microvascular bed parameters Rm,i and Cm,i obtained previously (S210).

Next, the boundary condition of each outlet of the CFD model is reset using the updated LPM model (S220). In order to reset the boundary condition of each outlet of the CFD model, first, a virtual LPM blood flow rate Qlpm,i estimated to flow to each branch of the updated LPM model is calculated. The virtual LPM blood flow rate Qlpm,i of the blood flowing through each branch is calculated using the total outflow blood flow rate Qtot_cfd of the CFD model obtained in step S190. The virtual LPM blood flow rate Qlpm,i of each branch is obtained by distributing the total outflow blood flow rate Qtot_cfd to each branch at a ratio inversely proportional to the microvascular bed resistance Rm,i of each branch obtained in step S200. The distribution of the total outflow blood flow rate Qtot_cfd at a rate inversely proportional to the updated microvascular bed resistance Rm,i is supported by Assumption 4. Assuming that the same pressure P0 acts on the upstream side of the microvascular bed connected to each branch and the same pressure Pv acts on the downstream side of the microvascular bed, the blood flow rate of the blood passing through each microvascular bed is inversely proportional to the resistance of the microvascular bed. That is, it can be noted from the relationship of Qi=(P0−Pv)/(Rm,i) that the blood flow rate of the blood passing through each microvascular bed is inversely proportional to the resistance.

When the virtual LPM blood flow rate Qlpm,i for each branch of the updated LPM model is obtained, the outlet boundary condition of the branch of the CFD model corresponding to each virtual LPM blood flow rate Qlpm,i is reset using the following Equation 15.

$$P_i = (R_{a,i} + R_{m,i}) \times Q_{lpm,i} \qquad (15)$$

In the above equation, Pi is the boundary condition blood pressure updated and set for the outlet of each branch of the CFD model, Ra,i is the artery resistance of the pre-set LPM model, Rm,i is the microvascular bed resistance of the LPM model updated by the CFD simulation, and Qlpm,i is the virtual LPM blood flow rate obtained by distributing the total outflow blood flow rate Qtot_cfd in inverse proportion to each updated LPM microvascular bed resistance Rm,i.

Next, the iterative performance index (iter) is increased (S230), the blood flow simulation for the CFD model having the updated boundary condition is performed again (S170), and steps S170 to S220 are repeatedly performed until the convergence condition of the simulation for the CFD model is satisfied (S180). The iterative performance index may set to have a limit so that steps S170 to S220 are repeated a predetermined number of iteration times. In addition, a time marching algorithm that makes use of an increment Δt of a constant time interval may be used as the repetitive performance index.

There may be various convergence conditions for determining whether the results of the repetitive CFD-LPM-coupled blood flow simulations described above have converged. For example, if the root mean square (RMS) error at each grid point of the calculated CFD model region is equal to or less than a predetermined value, it is determined that the convergence conditions are satisfied. Then, the blood flow information for the three-dimensional blood vessel model may be outputted (S240). The outputted blood flow information for the three-dimensional blood vessel model includes a pressure and a blood flow velocity.

In addition, the value of the microvascular bed parameters Rm,i and Cm,i of the LPM model updated by the CFD-LPM-coupled simulation and the value of the blood flow rate Qi of the blood flowing out to each branch are compared with the values of the previous steps. If the difference of the values is less than a predetermined value, it is determined that the convergence conditions are satisfied. Then, the blood flow information for the three-dimensional blood vessel model may be outputted (S240). In addition, the convergence conditions may be modified by applying the aforementioned convergence conditions individually or in an overlapped manner.

The most distinctive feature of the CFD-LPM-coupled blood flow simulation method according to the present invention from the conventional method is that the microvascular bed parameters of the LPM model are determined by the CFD simulation. Explaining again, the microvascular bed parameters are updated to become suitable for the blood flow rate of the blood flowing out of the branch according to the stenosis formed in the three-dimensional blood vessel model or the size and shape of the blood vessel, and the microvascular bed parameters are determined by repeatedly performing the blood flow simulation for the CFD model under the boundary conditions determined by the updated microvascular bed parameters. This hemodynamic simulation method is a method consistent with the physiological phenomenon that the hemodynamic characteristics of the microvascular bed are appropriately changed according to the hemodynamic state of the artery connected to the microvascular bed (the blood pressure at the end of the artery and the blood flow rate of the blood flowing out to the end of the artery).

Method of Obtaining Artery Parameters of LPM Model

Hereinafter, a method of obtaining the artery parameters of the LPM model will be described. The artery parameters of the LPM model are the hemodynamic characteristics of each blood vessel branch of the subject-specific blood vessel system, namely the resistance and compliance of the artery branch.

One of the methods of obtaining the hemodynamic characteristics of each artery branch is a method of measuring a blood flow rate of blood flowing through each branch. The blood flow rate of the blood flowing through each branch may be measured invasively or non-invasively. For example, a blood pressure or a blood flow rate may be directly measured by invasively inserting a guide wire into a blood vessel. Alternatively, a blood flow velocity may be measured using a four-dimensional medical imaging apparatus.

As a method of non-invasively obtaining the hemodynamic characteristics of each artery branch, there is a method of using the shape of a three-dimensional blood vessel model. For example, this is a method of estimating a blood flow rate of blood flowing to each branch by measuring the length of each branch of a three-dimensional blood vessel model. The method disclosed in Patent Document 4 may be used as the method of obtaining the hemodynamic characteristics of the artery blood vessel based on the length of the blood vessel.

Figure 11:
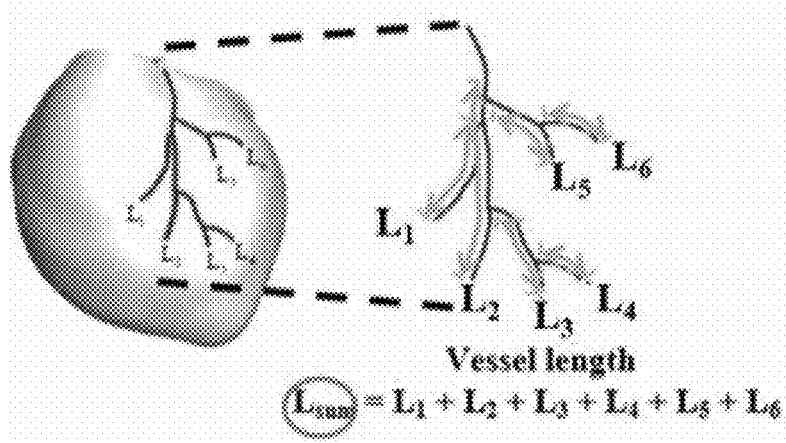
FIG. 11 is a schematic diagram of a method of obtaining hemodynamic characteristics of an arterial blood vessel based on a blood vessel length.
Figure 11:
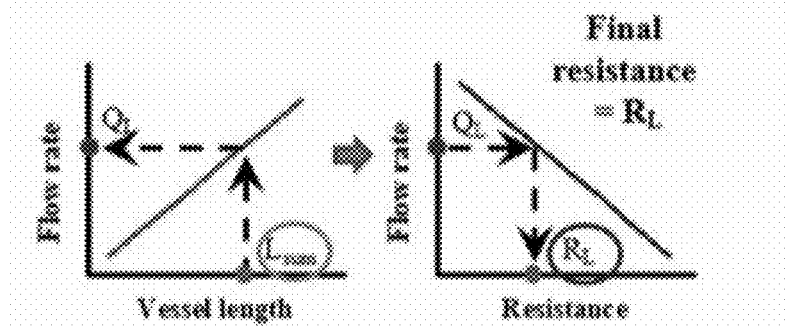

FIG. 11 is a schematic diagram of a method of obtaining hemodynamic characteristics of an artery blood vessel based on a blood vessel length. Referring to FIG. 11, the total blood vessel length Lsum is obtained by measuring each branch of a subject-specific three-dimensional coronary artery model, which is created with cardiac CT image data, as shown in FIG. 11. When obtaining a three-dimensional coronary artery model, it is desirable to ensure that the diameters of the ends of all branches are equal to or greater than a predetermined value. For example, it is preferable to set the diameters of the ends of the branches to 1 mm or more. Next, as shown in FIG. 11, the theoretical blood flow rate $Q_L$ corresponding to the total blood vessel length Lsum is obtained from a graph acquired by experiment as shown in FIG. 11. After the theoretical blood flow $Q_L$ is determined, the total resistance $R_L$ for the artery of the coronary artery system corresponding to the theoretical blood flow rate is obtained from a graph acquired by experiment as shown in FIG. 11. After the total resistance for the artery of the coronary artery system is obtained, the resistance of each branch is obtained by distributing the total resistance in an inverse proportion to the length of each branch.

Figure 12:
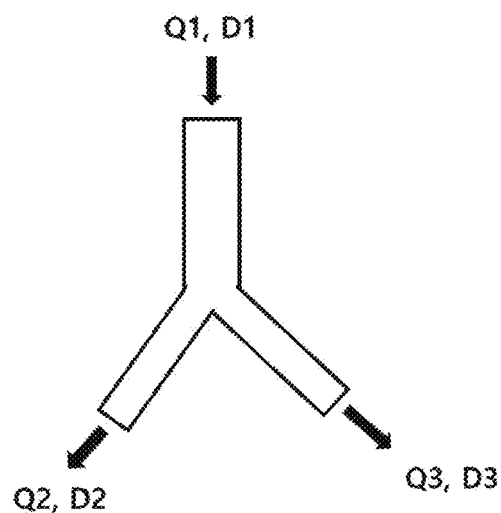
FIG. 12 is an explanatory diagram of a theoretical flow rate distribution according to the Murray's rule for blood vessel branches.

As the method of non-invasively obtaining the hemodynamic characteristics of the branch of the artery, there is another method that uses the shape of a three-dimensional blood vessel model. This is, for example, a method of estimating a blood flow rate of blood flow flowing to each branch by measuring the cross-sectional area of each branch of a three-dimensional blood vessel model. This method is based on the distribution of the theoretical flow rate according to the Murray's rule, and has been widely used in existing studies (Non-Patent Document 5). In this method, the theoretical flow rate is distributed to each branch according to the Murray's rule, and the resistance and compliance for each branch are determined based on the distributed theoretical flow rate. For example, when one large branch is divided into two small branches as shown in FIG. 12, the distribution of the theoretical flow rate for each branch can be obtained by using Equation 16 below.

$$Q_2 = \frac{D_2^{2.7}}{D_2^{2.7} + D_3^{2.7}} Q_1 \qquad (16)$$

$$Q_3 \frac{D_3^{2.7}}{D_2^{2.7} + D_3^{2.7}} Q_1$$

Method of Obtaining Artery Parameters of LPM Model by CFD-LPM-Coupled Simulation As the method of non-invasively obtaining the hemodynamic characteristics of the branch of the artery, there is another method of using the shape of a three-dimensional blood vessel model. For example, this is a method of obtaining the hemodynamic characteristics of the branch of the artery obtained by using a CFD-LPM-coupled blood flow simulation method as shown in FIG. 13.

The hemodynamic characteristics of the subject-specific blood vessel can be said to be determined by the shape and material of the blood vessel. That is, the resistance of a blood flow through the blood vessel can be said to be a characteristic of a blood vessel determined by the geometric shape and dimensions of the blood vessel. In addition, the compliance of the blood vessel can be said to be a characteristic of the blood vessel mainly determined by the elasticity of blood vessel. Furthermore, if the boundary condition of the CFD model in a specific state of a subject is known, the hemodynamic characteristics of the blood vessel branch of the CFD model, i.e., the resistance and compliance of the blood vessel branch, can be obtained by a blood flow simulation for the CFD model. Therefore, by setting the boundary condition of the CFD model in a specific state of a subject and performing a simulation on the subject-specific CFD model, it is possible to obtain the hemodynamic characteristics of the blood vessel determined by the shape of the subject-specific CFD model. In addition, even when the subject's state is changed from a resting state to a motion state, if the shape and physical properties of the blood vessel are not changed significantly, the resistance and compliance of the blood vessel against the blood flow will not be changed significantly. Even if the physical properties of the blood vessel are changed depending on the change in the motion state of the subject, according to the method according to the present invention, the change in the characteristics according to the change in the subject state is accommodated as a change in the microvascular bed parameters of the LPM model. Therefore, according to the method of the present invention, the artery parameters of the blood vessel for the resting state of the subject may be obtained and used as the artery parameters of the LPM model.

Figure 13:
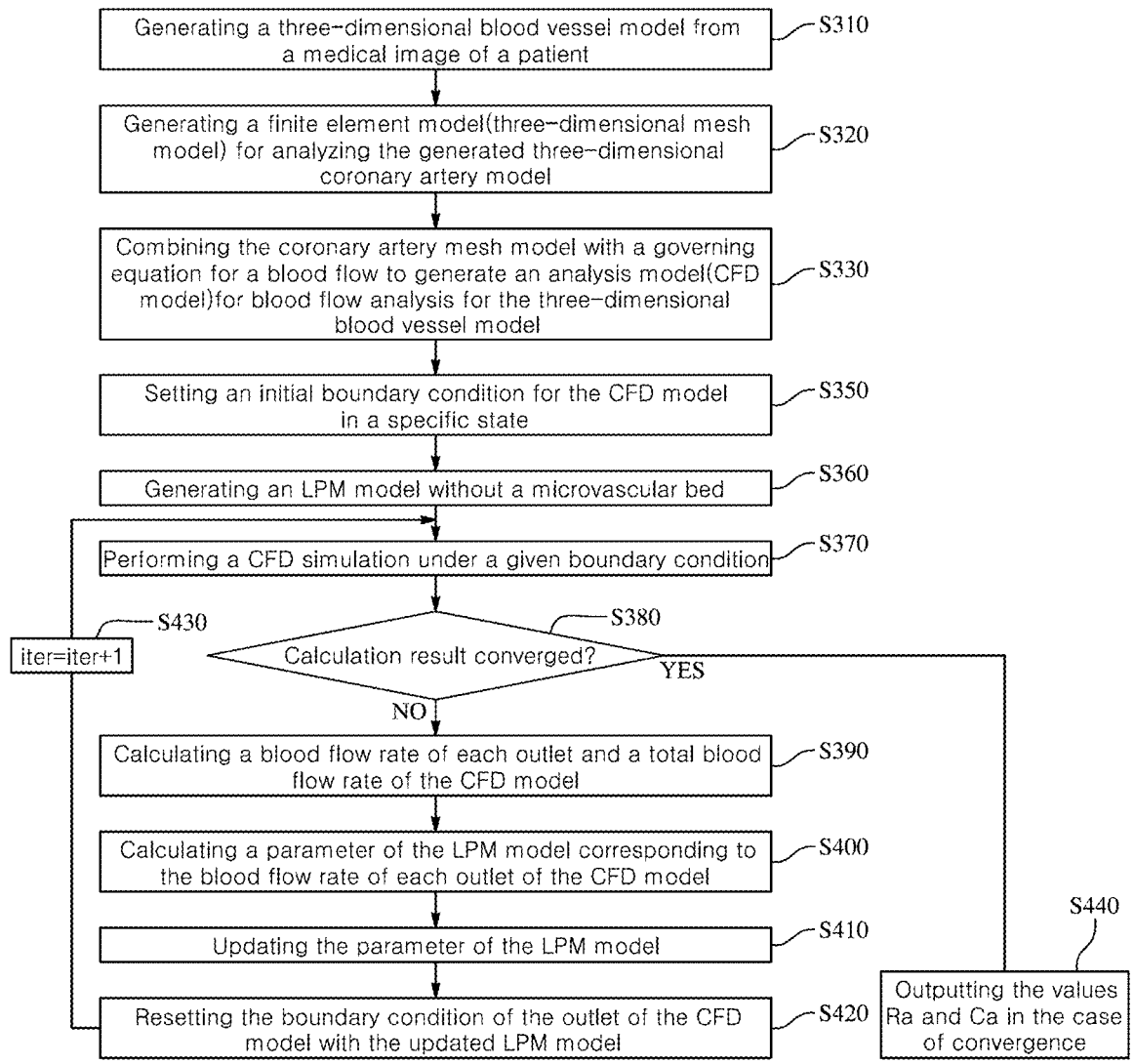
FIG. 13 is a flowchart of a method of obtaining artery parameters through the use of the novel CFD-LPM-coupled blood flow simulation method according to the present invention.

The method of obtaining the hemodynamic characteristics of the artery branch shown in FIG. 13 is different from the CFD-LPM-coupled blood flow simulation method shown in FIG. 9 in terms of two points.

Figure 14:
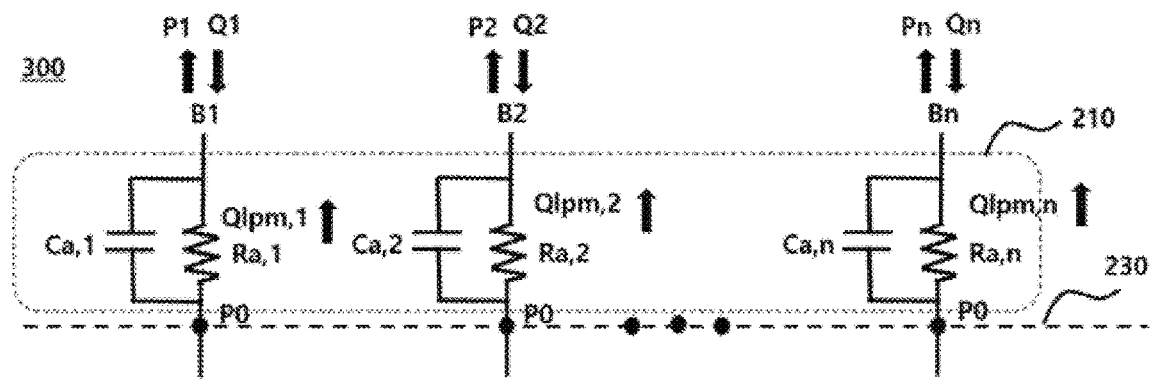
FIG. 14 is a schematic diagram of an example of an LPM model for obtaining artery parameters by applying the method shown in FIG. 13.

First, as shown in FIG. 14, an LPM model 300 composed of only artery parameters is used. Second, the CFD-LPM-coupled blood flow simulation is performed in a state in which all the blood pressures downstream of the artery parameters of each branch of the LPM model are fixed to the same blood pressure P0 in the CFD-LPM-coupled simulation.

Figure 15:
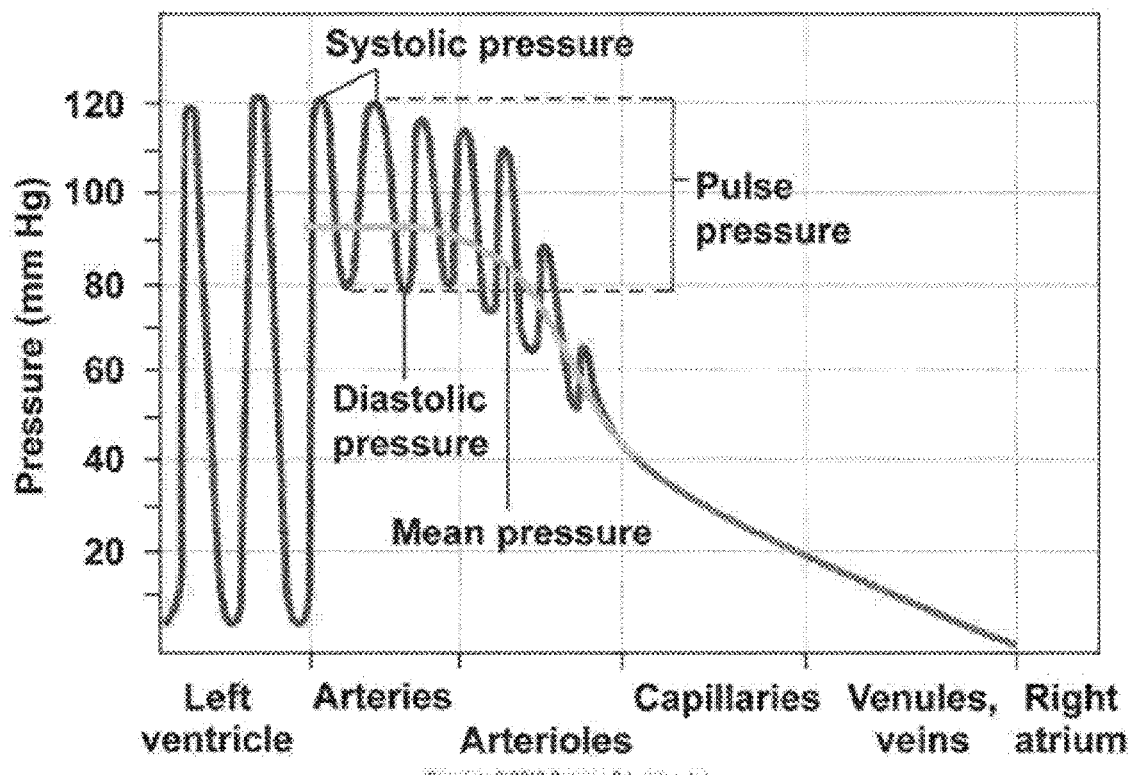
FIG. 15 is a graph showing changes in blood pressure for respective blood circulation vessels.

The blood pressure P0 is preferably set as the blood pressure when the subject is in a resting state. The blood pressure P0 when the subject is in the resting state may be set to a blood pressure in the range of 80%-95% of the blood pressure measured from the subject. FIG. 15 is a graph showing a change in blood pressure for each blood vessel according to blood circulation. Referring to FIG. 15, it can be seen that the average blood pressure of a blood flow in a blood circulation system has an almost constant value in the artery, and rapidly drops as the blood flow passes through the arterioles and capillaries. In other words, it can be noted that the blood flow resistance is very small because the average blood pressure is almost maintained in the artery, and further that the blood flow resistance is very large because the average pressure drop is rapidly generated in the capillary bed. Therefore, when the subject is in a resting state, it can be said that it is consistent with the physiological phenomenon even if the blood pressure P0 downstream of the arterial parameters is set to 80% to 95% of the measured blood pressure.

Hereinafter, the method shown in FIG. 13 will be described in detail with reference to FIG. 14. In the simulation for obtaining the artery parameters, the artery parameters of the LPM model shown in FIG. 14, which are linked to each branch of the CFD model, are not previously set, but are obtained by a CFD-LPM-coupled simulation performed in conformity with the shape of the CFD model.

In the example illustrated in FIG. 13, the processes (S310 to S330) of generating a three-dimensional blood vessel model, a three-dimensional mesh model and a CFD model by receiving a medical image of a subject's heart is the same as those described with reference to FIG. 9.

After the subject-specific CFD model is generated, the total blood flow rate and the total resistance when the subject is in a specific state are set (S340). When the specific state is set to a resting state, in the case of the heart as in the present example, the total blood flow rate (theoretical blood flow rate, Qtot) may be set to 4% of the subject's cardiac output. In the case of cerebral blood vessel, the blood flow rate is set to about 15% of the cardiac output. The total resistance may be obtained by Rtot=(Pao-P0)/Qtot.

Next, in order to analyze the analysis model, the initial conditions at the grid points of the analysis model and the boundary conditions of the inlet and the outlet are determined (S350).

Next, an LPM model for determining the boundary condition of the outlet of the CFD model is generated (S360). As the LPM model, a model composed of only artery parameters without microvascular bed parameters is used as shown in FIG. 14.

Next, a CFD-LPM-coupled simulation is performed to obtain the artery parameters Ra and Ca of the LPM model. Before performing the CFD-LPM-coupled simulation, a reference branch is selected from the three-dimensional coronary artery model.

Next, a simulation for the CFD model is performed under a given boundary condition (S370). The blood pressure Pao measured from a subject is set as the inlet boundary condition of the CFD model, and the boundary condition of the outlet of each branch of the CFD model may be arbitrarily set. For the sake of convenience, it is preferable to set the same blood pressure equal to or greater than 50% of the measured blood pressure as the pressure boundary condition of the outlet.

Next, the outflow blood flow rate Qi of the blood flowing out through the outlet of each branch is obtained from the simulation results for the CFD model under the predetermined initial condition and the boundary condition, and the sum of the blood flow rate of the blood flowing out to each branch, i.e., the total outflow blood flow rate Qtot_cfd is obtained (S390). In this regard, i is the index of the branch.

Next, the artery parameters $R_{a,i}$ and $C_{a,i}$ of each branch are calculated using the outflow flow rate Qi of each outlet of the CFD model (S400). First, the blood flow rate of the blood flowing out through each outlet of the CFD model is applied to Equation 12 to obtain the artery compliance $C_{a,i}$ of each branch. In addition, the artery resistance $R_{a,i}$ of each branch is obtained using the artery compliance $C_{a,i}$ of each branch and the artery compliance $C_{a,ref}$ of the reference branch selected previously. First, the resistance $R_{a,ref}$ of the reference branch is obtained using Equation 10, and then the remaining microvascular bed resistance $R_{a,i}$ is obtained using Equation 8.

Next, the artery parameters of the LPM model are updated with the previously obtained artery parameters $R_{a,i}$ and $C_{a,i}$ (S410).

Next, the boundary condition of each outlet of the CFD model is reset using the updated LPM model (S420). In order to reset the boundary condition of each outlet of the CFD model, the virtual LPM blood flow rate $Q_{lpm,i}$ of the blood expected to flow through each branch of the updated LPM model is first estimated. The virtual LPM blood flow rate $Q_{lpm,i}$ of the blood expected to flow through each branch is calculated using the total outflow blood flow rate Qtot_cfd of the CFD model obtained in step S390. The virtual LPM blood flow rate $Q_{lpm,i}$ at each branch is obtained by distributing the total outflow blood flow rate Qtot-cfd to the respective branches at a ratio inversely proportional to the artery resistance $R_{a,i}$ of each branch obtained in step S400.

After the virtual LPM blood flow rate $Q_{lpm,i}$ for each branch of the updated LPM model is obtained, the boundary condition of the outlet of the branch of the CFD model corresponding to each virtual LPM blood flow rate $Q_{lpm,i}$ is reset using Equation 15. At this time, the microvascular bed resistance $R_{m,i}$ is set to 0 in Equation 15.

Next, the iterative performance index iter is increased (S430), the blood flow simulation for the CFD model is performed using the updated boundary condition (S370), and steps S170 to S220 are repeatedly performed until the convergence condition of the simulation for the CFD model is satisfied (S380). There may be various convergence conditions for determining whether the results of the repetitive CFD-LPM-coupled blood flow simulation as described above have converged. For example, if the root mean square (RMS) error at each grid point of the calculated CFD model region is equal to or less than a predetermined value, it is determined that the convergence condition is satisfied. Then, values $R_{a,i}$ and $C_{a,i}$ are outputted (S440).

Furthermore, the value of the microvascular bed parameters $R_{a,i}$ and $C_{a,i}$ of the LPM model updated by the CFD-LPM-coupled simulation and the value of the blood flow rate Qi of the blood flowing out to each branch are compared with the values of the previous steps. If the difference of the values is less than a predetermined value, it is determined that the convergence conditions are satisfied. Then, values $R_{a,i}$ and $C_{a,i}$ for each artery branch may be outputted (S440). In addition, the convergence conditions may be modified by applying the aforementioned convergence conditions individually or in an overlapped manner.

When the blood flow simulation is performed on the three-dimensional blood vessel model for the subject-specific blood vessel by the method described above, the blood pressure and the blood flow velocity for the three-dimensional blood vessel model are obtained. Furthermore, using the blood pressure and the blood flow velocity calculated by the simulation, it is possible to obtain the blood flow rate of the blood flowing through each branch, the wall shear stress WSS, the resistance and compliance for each branch of the blood vessel, and the resistance and compliance of the microvascular bed. In addition, using the simulation results, it is also possible to calculate the hemodynamic quantities of interest for various subject-specific coronary arteries. The hemodynamic quantities of interest include, for example, the coronary artery fractional flow reserve (FFR), the coronary flow reserve (CFR), the index of microvascular resistance (BAR), the instantaneous wave-free ratio (IFR), the basal Pd/Pa, the basal stenosis resistance, the hyperemic stenosis resistance, and the like.

What is claimed is:
1. A blood flow simulation method for a subject-specific three-dimensional blood vessel model, comprising:
(a) receiving the subject-specific three-dimensional blood vessel model;
(b) generating a computational fluid dynamics (CFD) model for blood flow analysis by applying a blood flow equation to the subject-specific three-dimensional blood vessel model;
(c) setting an initial condition and a boundary condition in the CFD model;
(d) generating an lumped parameter (LPM) model including artery parameters and microvascular bed parameters to provide an outlet boundary condition of the CFD model; and
(e) performing a blood flow simulation for the CFD model by coupling the CFD model and the LPM model,
wherein the act of (e) performing the blood flow simulation for the CFD model by coupling the CFD model and the LPM model includes:
(f) performing a blood flow simulation for the CFD model under the initial condition and the boundary condition;
(g) calculating a blood flow rate Qi and a total outflow blood flow rate Qtot_cfd for each outlet of the CFD model by the blood flow simulation;
(h) updating the microvascular bed parameters of the LPM model by using the blood flow rate for each outlet and the total outflow blood flow rate of the CFD model;
(i) updating the boundary condition of the outlet of each branch of the CFD model by using the updated LPM model; and
(j) repeatedly performing the acts of (f) to (i) until a convergence condition of the blood flow simulation for the CFD model is satisfied.

2. The method of claim 1, wherein the artery parameters and the microvascular bed parameters of the LPM model are connected in series,
the artery parameters include an artery resistance Ra and an artery compliance Ca connected in parallel, and the microvascular bed parameters include a microvascular bed resistance Rm and a microvascular bed compliance Cm connected in parallel.

3. The method of claim 2, wherein the artery parameters have parameter values determined by using a length of a branch of the subject-specific three-dimensional blood vessel model.

4. The method of claim 2, wherein the artery parameters have parameter values determined by using a diameter of a branch end of the subject-specific three-dimensional blood vessel model.

5. The method of claim 2, wherein the artery parameters have parameter values determined by a CFD-LPM-coupled simulation for the subject-specific three-dimensional blood vessel model,
the LPM model used in the CFD-LPM-coupled simulation for determining the artery parameters is an LPM model including only the artery parameters, and
a pressure condition in a resting state of a subject is used as a pressure condition downstream of the artery parameters of the LPM model in the CFD-LPM-coupled simulation.

6. The method of claim 1, wherein in the act of (h) updating the microvascular bed parameters of the LPM model by using the blood flow rate for each outlet of the CFD model and the total outflow blood flow rate of the CFD model,
a microvascular bed compliance parameter $C_{m,i}$ of the LPM model is updated by a value obtained using the following equation that approximates a value obtained by dividing an outflow blood flow rate $Q_i$ of an outlet of each branch obtained through a CFD model simulation by a difference between a systolic blood pressure and a diastolic blood pressure measured from a subject and multiplying the outflow blood flow rate $Q_i$ by a heart rate cycle:

$$C_{m,i} = \left(\frac{dV/dt}{dP/dt}\right)_i \sim \frac{Q_i}{\Delta P_i/\Delta \tau}$$

where $Q_i$ is a blood flow rate in an i-th branch and $\Delta P_i/\Delta \tau$ represents a pressure change over time in the i-th branch, and
a microvascular bed resistance parameter $R_{m,i}$ of each branch is updated by a value obtained by obtaining a microvascular bed resistance $R_{m,ref}$ of a selected reference branch through the use of an equation:

$$R_{m,ref} = (R_{tot} - R_{a,tot})\left(1 + \sum_{\substack{i=1 \\ i \neq ref}}^{n} \frac{C_{m,i}}{C_{m,ref}}\right)$$

and by using an equation:

$$R_{m,1}C_{m,1} = R_{m,2}C_{m,2} = \ldots = R_{m,n}C_{m,n}$$

which indicates a condition that the product of the microvascular bed resistance $R_{m,ref}$ of the selected reference branch and the microvascular bed compliance $C_{m,ref}$ of the reference branch is equal to the product of the microvascular bed resistance $R_{m,i}$ and the microvascular bed compliance $C_{m,i}$ of the remaining branches.

7. The method of claim 6, wherein in the act of (i) updating the boundary condition of the outlet of each branch of the CFD model by using the updated LPM model, the blood pressure set as the boundary condition of the outlet of each branch of the CFD model is a blood pressure obtained using an equation:

$$P_i = (R_{a,i} + R_{m,i}) \times Q_{lpm,i}$$

where $P_i$ is a boundary condition blood pressure updated and set for the outlet of each branch of the CFD model, $R_{a,i}$ is an artery resistance of a pre-set LPM model, $R_{m,i}$ is a microvascular bed resistance of the LPM model updated by the CFD simulation, and $Q_{lpm,i}$ is a virtual LPM blood flow rate obtained by distributing the total outflow blood flow rate $Q_{tot\_cfd}$ in inverse proportion to each updated LPM microvascular bed resistance $R_{m,i}$.

8. A blood flow simulation apparatus for a subject-specific three-dimensional blood vessel model, comprising:
a processor; and
a memory in which a computer program to be executed in the processor is stored
wherein the computer program is configured to perform:
(a) receiving the subject-specific three-dimensional blood vessel model;
(b) generating a computational fluid dynamics (CFD) model for blood flow analysis by applying a blood flow equation to the subject-specific three-dimensional blood vessel model;
(c) setting an initial condition and a boundary condition in the CFD model;
(d) generating an lumped parameter (LPM) model including artery parameters and microvascular bed parameters to provide an outlet boundary condition of the CFD model; and
(e) performing a blood flow simulation for the CFD model by coupling the CFD model and the LPM model,
wherein the act of (e) performing the blood flow simulation for the CFD model by coupling the CFD model and the LPM model includes:
(f) performing a blood flow simulation for the CFD model under the initial condition and the boundary condition;
(g) calculating a blood flow rate $Q_i$ and a total outflow blood flow rate $Q_{tot\_cfd}$ for each outlet of the CFD model by the blood flow simulation;
(h) updating the microvascular bed parameters of the LPM model by using the blood flow rate for each outlet and the total outflow blood flow rate of the CFD model;
(i) updating the boundary condition of the outlet of each branch of the CFD model by using the updated LPM model; and
(j) repeatedly performing the acts of (f) to (i) to calculate at least one hemodynamic physical quantity until a convergence condition of the blood flow simulation for the CFD model is satisfied.

9. The apparatus of claim 8, wherein the artery parameters and the microvascular bed parameters of the LPM model are connected in series,
the artery parameters include an artery resistance Ra and an artery compliance Ca connected in parallel, and
the microvascular bed parameters include a microvascular bed resistance Rm and a microvascular bed compliance Cm connected in parallel.

10. The apparatus of claim 9, wherein the artery parameters have parameter values determined by using a length of a branch of the subject-specific three-dimensional blood vessel model.

11. The apparatus of claim 9, wherein the artery parameters are parameter values determined by a CFD-LPM-coupled simulation for the subject-specific three-dimensional blood vessel model, the LPM model used in the CFD-LPM-coupled simulation for determining the artery parameters is an LPM model including only the artery parameters, and a pressure condition in a resting state of a subject is used as a pressure condition downstream of the artery parameters of the LPM model in the CFD-LPM-coupled simulation.

12. The apparatus of claim 8, wherein in the act of (h) updating the microvascular bed parameters of the LPM model by using the blood flow rate for each outlet of the CFD model and the total outflow blood flow rate of the CFD model, a microvascular bed compliance parameter $C_{m,i}$ of the LPM model is updated by a value obtained using the following equation that approximates a value obtained by dividing an outflow blood flow rate $Q_i$ of an outlet of each branch obtained through a CFD model simulation by a difference between a systolic blood pressure and a diastolic blood pressure measured from a subject and multiplying the outflow blood flow rate $Q_i$ by a heart rate cycle:

$$C_{m,i} = \left(\frac{dV/dt}{dP/dt}\right)_i \sim \frac{Q_i}{\Delta P_i / \Delta \tau}$$

where $Q_i$ is a blood flow rate in an i-th branch and $\Delta P_i/\Delta \tau$ represents a pressure change over time in the i-th branch, and a microvascular bed resistance parameter $R_{m,i}$ of each branch is updated by a value obtained by obtaining a microvascular bed resistance $R_{m,ref}$ of a selected reference branch through the use of an equation:

$$R_{m,ref} = (R_{tot} - R_{a,tot})\left(1 + \sum_{\substack{i=1 \\ i \neq ref}}^{n} \frac{C_{m,i}}{C_{m,ref}}\right)$$

and by using an equation:

$$R_{m,1}C_{m,1} = R_{m,2}C_{m,2} = \ldots = R_{m,n}C_{m,n}$$

which indicates a condition that the product of the microvascular bed resistance $R_{m,ref}$ of the selected reference branch and the microvascular bed compliance $C_{m,ref}$ of the reference branch is equal to the product of the microvascular bed resistance $R_{m,i}$ and the microvascular bed compliance $C_{m,i}$ of the remaining branches.

13. The apparatus of claim 12, wherein in the act of (i) updating the boundary condition of the outlet of each branch of the CFD model by using the updated LPM model, the blood pressure set as the boundary condition of the outlet of each branch of the CFD model is a blood pressure obtained using an equation:

$$P_i(R_{a,i}+R_{m,i}) \times Q_{lpm,i},$$

where $P_i$ is a boundary condition blood pressure updated and set for the outlet of each branch of the CFD model, $R_{a,i}$ is an artery resistance of a pre-set LPM model, $R_{m,i}$ is a microvascular bed resistance of the LPM model updated by the CFD simulation, and $Q_{lpm,i}$ is a virtual LPM blood flow rate obtained by distributing the total outflow blood flow rate $Q_{tot\_cfd}$ in inverse proportion to each updated LPM microvascular bed resistance $R_{m,i}$.

* * * * *